(12) United States Patent
Aoi et al.

(10) Patent No.: US 7,619,374 B2
(45) Date of Patent: Nov. 17, 2009

(54) RADIOTHERAPY SYSTEM FOR PERFORMING RADIOTHERAPY WITH PRESICE IRRADIATION

(75) Inventors: Tatsufumi Aoi, Hiroshima (JP); Kuniyuki Kajinishi, Hiroshima (JP); Ichiro Yamashita, Hiroshima (JP); Shinji Nomura, Hiroshima (JP); Yoshio Sugimoto, Hiroshima (JP); Susumu Urano, Hiroshima (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 11/987,808

(22) Filed: Dec. 4, 2007

(65) Prior Publication Data

US 2008/0267352 A1   Oct. 30, 2008

(30) Foreign Application Priority Data

Jan. 16, 2007 (JP) ............................ 2007-007331
Jan. 16, 2007 (JP) ............................ 2007-007341

(51) Int. Cl.
*H01J 23/00* (2006.01)

(52) U.S. Cl. .................. 315/500; 315/505; 315/39; 315/39.55; 378/64; 378/65; 600/427

(58) Field of Classification Search .................. 378/64, 378/65, 68, 143–145, 195–197; 315/5.41, 315/5.46, 500, 501, 505, 507, 39, 39.55; 600/424, 427

See application file for complete search history.

(56) References Cited

U.S. PATENT DOCUMENTS

| | | | |
|---|---|---|---|
| 3,820,035 A | 6/1974 | Meddaugh | |
| 4,121,173 A | 10/1978 | Azam et al. | |
| 4,656,394 A | 4/1987 | Perraudin | |
| 4,713,581 A * | 12/1987 | Haimson | 315/5.41 |
| 5,087,887 A | 2/1992 | Kawakami | |
| 6,844,689 B1 | 1/2005 | Brown et al. | |
| 6,977,987 B2 * | 12/2005 | Yamashita et al. | 378/64 |
| 7,085,347 B2 * | 8/2006 | Mihara et al. | 378/65 |
| 7,208,890 B2 * | 4/2007 | Zavadtsev et al. | 315/500 |

FOREIGN PATENT DOCUMENTS

| | | |
|---|---|---|
| EP | 0 702 982 A2 | 3/1996 |
| JP | 50-105048 A | 8/1975 |
| JP | 62-206798 A | 9/1987 |
| JP | 8-206103 A | 8/1996 |
| JP | 2001-9050 A | 1/2001 |
| JP | 2002-253687 A | 9/2002 |
| JP | 2003-100243 A | 4/2003 |
| JP | 2005-33463 A | 2/2005 |
| JP | 3746744 B2 | 12/2005 |
| WO | WO 00/14785 A2 | 4/2000 |
| WO | WO 03/018131 A1 | 3/2003 |

* cited by examiner

*Primary Examiner*—Haissa Philogene
(74) *Attorney, Agent, or Firm*—Birch, Stewart, Kolasch & Birch, LLP

(57) ABSTRACT

A radiotherapy system includes: a waveguide, an adjustable waveguide, and a non-reciprocal circuit element. The waveguide transmits a high-frequency wave from a high-frequency power source to an acceleration tube. The adjustable waveguide is included in said waveguide and transforms a part of said waveguide. The non-reciprocal circuit element is provided between said acceleration tube and said adjustable waveguide in said waveguide. Said acceleration tube accelerates charged particles for generating therapeutic radiation by using said high-frequency wave.

15 Claims, 16 Drawing Sheets

RADIOTHERAPY SYSTEM FOR PERFORMING RADIOTHERAPY WITH PRESICE IRRADIATION

BACKGROUND OF THE INVENTION

1. Field of the Invention

The present invention relates to a radiotherapy system, and more particularly relates to a radiotherapy system for performing radiotherapy with precise irradiation.

2. Description of Related Art

A radiotherapy is known which a patient is treated by radiating a therapeutic radiation to an affected area (tumor). As the therapeutic radiation, a radiation generated by the bremsstrahlung is shown as an example. The radiotherapy is desired to more precisely irradiate the affected area with a predetermined dose of the therapeutic radiation, and change of energy (energy distribution) and intensity of the therapeutic radiation is desired to be smaller.

Japanese Laid-Open Patent Application JP-P2005-033463A discloses a waveguide rotary joint which needs no chalk construction requiring mechanical accuracy, and can thereby suppress attenuation of electromagnetic wave in a circular waveguide and reduce possibility of discharging from the circular waveguide. In the waveguide rotary joint to which a square waveguide is connected at respective end parts of the circular waveguide having a rotary coupling part whose both end parts can rotate relatively around a center line of axis, the waveguide rotary joint is characterized by converting an electromagnetic wave transmitted in TE10 mode inside an input side square waveguide into that in TE01 mode in a connection part with the above mentioned input side square waveguide and the above mentioned circular waveguide and transmitting it inside the circular waveguide, and converting the above mentioned electromagnetic wave from the TE01 mode into the TE10 mode again in a connection part with the above mentioned circular waveguide and an output side square waveguide and outputting it to the above mentioned output side square waveguide.

Japanese Patent JP 3746744B discloses a radiotherapy apparatus with superior treatment performance. The radiotherapy apparatus is characterized by including: a radiation head, a supporting and moving mechanism, a microwave generator, and a waveguide part. The radiation head has a therapeutic radiation generation part composed of an electron gun, a linear accelerator, and a target and a gimbal mechanism for oscillating the therapeutic radiation generation part. The supporting and moving mechanism is for supporting and moving this radiation head on a predetermined spherical coordinates. The microwave generator is for generating microwave to be supplied for this head, which is arranged on a static position. In the waveguide part, one end part is electromagnetically connected to the microwave generator and another end part is electromagnetically connected to the linear accelerator. A waveguide of said waveguide part mounted on said gimbal mechanism and a waveguide of said waveguide part from said microwave generator are connected by a flexible waveguide.

Japanese Laid-Open Patent Application JP-A-Showa, 62-206798 discloses a linear accelerator which is small sized, inexpensive, and high-precision, realized by mounting an extremely small sized and light-weighted acceleration tube on the acceleration body and by connecting the acceleration tube to a microwave source with a flexible waveguide. The linear accelerator is characterized in that the linear accelerator body is connected to the microwave source with the stretchable and flexible waveguide so as to rotate and move in upward and downward direction.

Japanese laid-Open patent Application JP-P2001-009050A discloses a radiotherapy device. In the radiotherapy device, the electron beams which are made incident to the magnetic field range of the second main electromagnet is deflected by 180 deg., and draws a second circular arcuate orbit. The electron beams along the second orbit is deflected by 180 deg. by the first main electromagnet and passes through a circular arcuate orbit to be emitted to a linear accelerator and is accelerated by the linear accelerator again. Mass is increased in the electron beams in this case so that the third orbit being the larger circular arcuate one is drawn when 180 deg. deflection is obtained by the second main electromagnet 107. The electron beams are deflected by a deflection magnet, a target is irradiated with them, X-rays are generated, a visual field range is restricted by a collimator and a testee body set on a diagnosing device is irradiated with the electron beams.

Japanese Laid-Open Patent Application JP-A-Showa, 50-105048 discloses a high frequency coupler. The high frequency coupler includes a first waveguide part, a co-axial waveguide, and a second waveguide part. The first waveguide part has at least one high frequency coupling window with a slit shape opened on a tube wall of the waveguide in a direction parallel to a tube axis direction of the waveguide. The co-axial waveguide is coupled with a window formed in a short-circuit board at an end of the first waveguide part along an extension of the tube axis direction, and a part of a central conductor thereof is inserted into the first waveguide part through the window. The second waveguide part has a tube axis direction approximately perpendicular to that of the first waveguide part and is provided opposite the first waveguide behind the co-axial waveguide.

Japanese laid-Open patent Application JP-P2002-253687A discloses a radiotherapeutic apparatus. In the radiotherapeutic apparatus, the head part which is positioned with a manipulator and irradiates a site to be treated of a patient with X rays is provided with an X-ray generator which accelerates electrons from an electron gun by microwaves and hits a target to generate the X rays. A microwave source for supplying the microwaves used for the acceleration of the electrons is provided on the side of the base part of the manipulator. The head part and the microwave source are connected with a waveguide.

SUMMARY OF THE INVENTION

An object of the present invention is to provide a radiotherapy system for controlling a dose of radiation with higher-precision.

Another object of the present invention is to provide a radiotherapy system for reducing change of energy (energy distribution) of a radiation.

Another object of the present invention is to provide a radiotherapy system for reducing change of intensity of a radiation.

Another object of the present invention is to provide a radiotherapy system for reducing the change of energy (energy distribution) of the radiation when a direction of the irradiation is changed.

Another object of the present invention is to provide a radiotherapy system for reducing the change of intensity of the radiation when a direction of the irradiation is changed.

This and other objects, features and advantages of the present invention will be readily ascertained by referring to the following description and drawings.

In order to achieve an aspect of the present invention, the present invention provides a radiotherapy system including: a waveguide, an adjustable waveguide, and a non-reciprocal circuit element. The waveguide transmits a high frequency wave from a high frequency wave source to an acceleration tube. The adjustable waveguide is included in the waveguide and transforms a part of the waveguide. The non-reciprocal circuit element is provided between the acceleration tube and the adjustable waveguide in the waveguide. The acceleration tube accelerates charged particles for generating therapeutic radiation by using the high frequency wave.

In the radiotherapy system, the adjustable waveguide may include a rotary joint in which one end is rotatable against another end.

In the radiotherapy system, the non-reciprocal circuit element may include a circulator.

The radiotherapy system may further include: another adjustable waveguide, and another non-reciprocal circuit element. The other adjustable waveguide is included in the waveguide and transforms another part of the waveguide between the part and the high frequency wave source. The other non-reciprocal circuit element is provided between the part and the another part in the waveguide.

The radiotherapy system may further include: another adjustable waveguide, and another non-reciprocal circuit element. The other adjustable waveguide is included in the waveguide and transforms another part of the waveguide between the part and the high frequency wave source. The other non-reciprocal circuit element is provided between the another part of the waveguide and the high frequency wave source in the waveguide.

The radiotherapy system may further include: an apparatus, and a control apparatus. The apparatus outputs a status of the waveguide. The control apparatus controls the high frequency wave source such that a high-frequency power is supplied to the acceleration tube based on the status.

In order to achieve another aspect of the present invention, the present invention provides an acceleration apparatus including: a waveguide, an adjustable waveguide, and a circulator. The waveguide transmits a high frequency wave from a high frequency wave source to an acceleration tube. The adjustable waveguide is included in the waveguide and transforms a part of the waveguide. The circulator is provided between the acceleration tube and the adjustable waveguide in the waveguide. The acceleration tube accelerates charged particles by using the high frequency wave.

In order to achieve another aspect of the present invention, the present invention provides a radiotherapy system including: an apparatus, and a control apparatus. The apparatus outputs a status of a waveguide which transmits a high frequency wave from a high frequency wave source to an acceleration tube. The control apparatus controls the high frequency wave source such that a high-frequency power is supplied to the acceleration tube based on the status. The acceleration tube accelerates charged particles for generating therapeutic radiation by using the high frequency wave.

In the radiotherapy system, the waveguide may include: an adjustable waveguide configured to transform a part of the waveguide.

In the radiotherapy system, the status may include: a shape of the waveguide.

In the radiotherapy system, the adjustable waveguide may include: a rotary joint configured to have one end rotatable against another end. The status may include: an angle between the one end and the another end.

In the radiotherapy system, the adjustable waveguide may include: a first adjustable waveguide, and a second adjustable waveguide. The status may include: a shape of the first adjustable waveguide, and a shape of the second adjustable waveguide.

In the radiotherapy system, the status may include: a high-frequency power supplied to the acceleration tube.

In the radiotherapy system, the status may include: a shape of the waveguide.

In the radiotherapy system, the apparatus may measure the status and output the measured status.

The radiotherapy system may further include: a driving apparatus configured to move the acceleration tube.

The apparatus further controls the driving apparatus based on the status.

In order to achieve another aspect of the present invention, the present invention provides an acceleration apparatus including: an apparatus, and a control. The apparatus outputs a status of a waveguide which transmits a high frequency wave from a high frequency wave source to an acceleration tube. The control apparatus controls the high frequency wave source such that a high-frequency power is supplied to the acceleration tube based on the status. The acceleration tube accelerates charged particles by using the high frequency wave.

DESCRIPTION OF THE PREFERRED EMBODIMENTS

Figure 1:
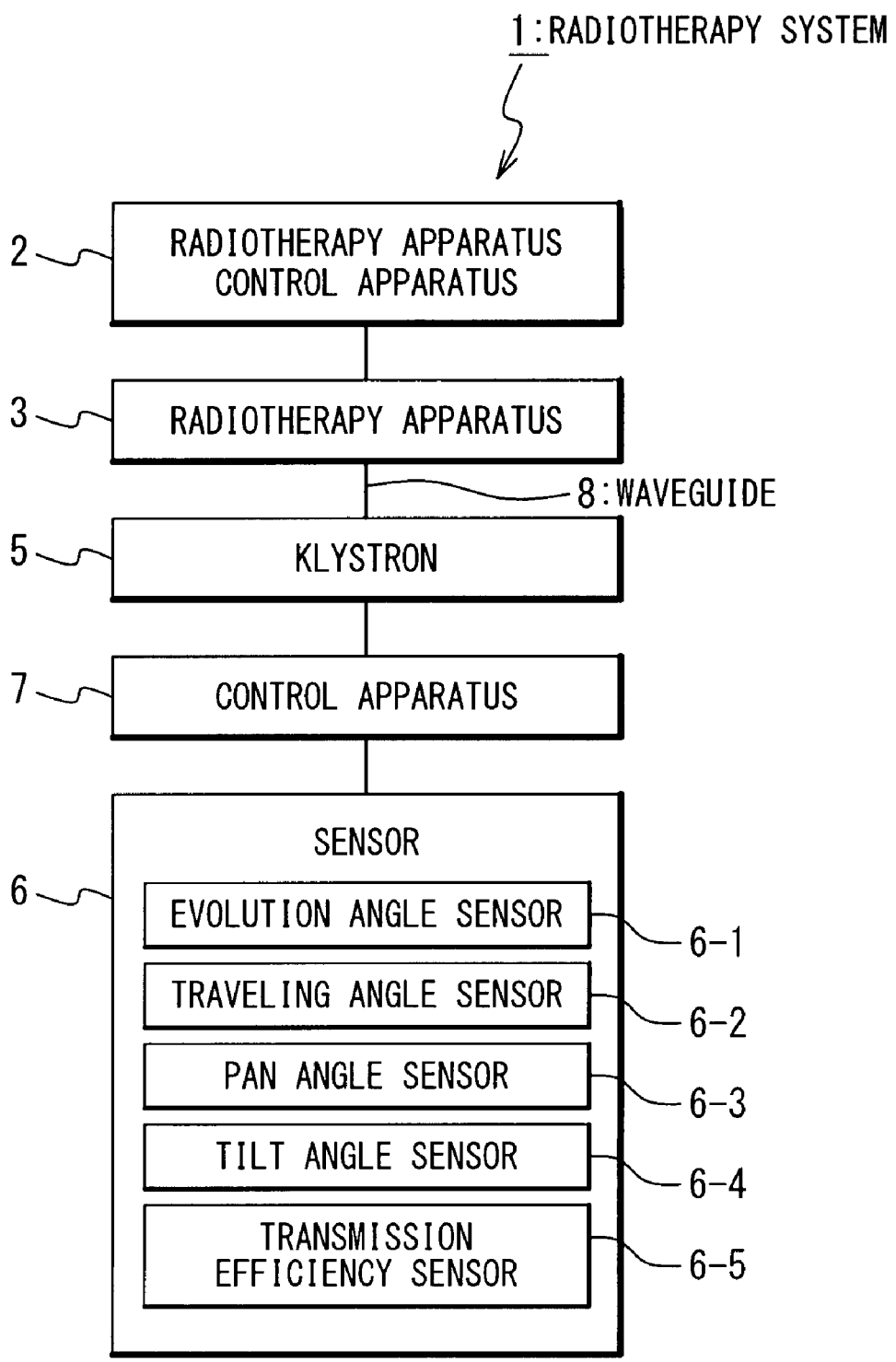
FIG. 1 is a block diagram showing an embodiment of a radiotherapy system according to the present invention.

Referring to drawings, an embodiment of a radiotherapy system according to the present invention will be described. As shown in FIG. 1, the radiotherapy system 1 includes a radiotherapy apparatus control apparatus 2, a radiotherapy apparatus 3, a klystron 5, a sensor 6, and a control apparatus 7. The radiotherapy apparatus control apparatus 2 is a computer exemplified as a personal computer. The radiotherapy apparatus control apparatus 2 is connected to the radiotherapy apparatus 3 so as to realize bidirectional communication. The klystron 5 generates a predetermined high-frequency power through a control of an oscillation RF intensity, a klystron acceleration voltage, and a klystron electric current by the control apparatus 7 and outputs the high frequency wave to the radiotherapy apparatus 3 via a waveguide 8. Meanwhile, a control target does not necessarily include all the three items, and it may include a part of or all of them. The respective control targets described below are the same as that described above as far as they are especially described. The sensor 6 is an apparatus for measuring a status of the waveguide 8. The apparatus includes an evolution angle sensor 6-1, a traveling angle sensor 6-2, a pan angle sensor 6-3, a tilt angle sensor 6-4, and a transmission efficiency sensor 6-5. The control apparatus 7 controls the klystron 5 based on a status measured by the sensor 6.

Figure 2:
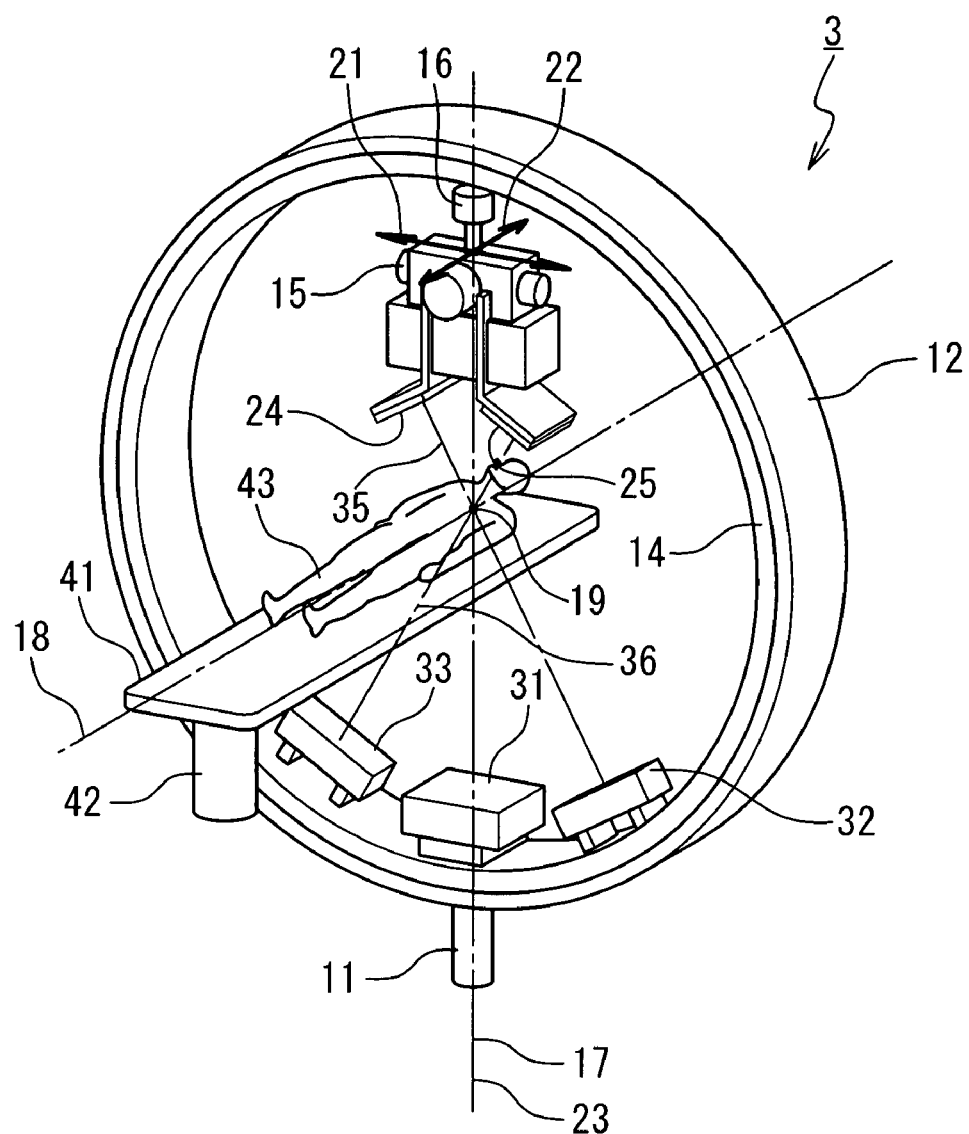
FIG. 2 is a perspective view showing a radiotherapy apparatus in the embodiment.

FIG. 2 shows the radiotherapy apparatus 3. The radiotherapy apparatus 3 includes an evolution driving apparatus 11, an O-ring 12, a traveling gantry 14, an head swing mechanism 15, and a therapeutic radiation irradiation apparatus 16. The evolution driving apparatus 11 supports the O-ring 12 rotatably centering around a rotation axis 17 on a base, and rotates the O-ring 12 centering around the rotation axis 17 being controlled by the radiotherapy apparatus control apparatus 2. The rotation axis 17 is parallel with the vertical direction. The O-ring 12 is formed in a ring shape centering around a rotation axis 18, which supports the traveling gantry 14 rotatably centering around the rotation axis 18. The rotation axis 18 is vertical to a vertical direction and passes an isocenter 19 included in the rotation axis 17. The rotation axis 18 is further secured against the O-ring 12, that is, rotates with the O-ring 12 centering around the rotation axis 17. The traveling gantry 14 is formed in a ring shape centering around the rotation axis 18, and arranged so as to be in a concentric fashion with the ring of the O-ring 12. The radiotherapy apparatus 3 further includes a traveling driving apparatus not shown in the drawing. The traveling driving apparatus rotates the traveling gantry 14 centering around the rotation axis 18 being controlled by the radiotherapy apparatus control apparatus 2.

The head swing mechanism 15 is secured inside the ring of the traveling gantry 14, and supports the therapeutic radiation irradiation apparatus 16 on the traveling gantry 14 so that the therapeutic radiation irradiation apparatus 16 can be arranged inside the traveling gantry 14. The head swing mechanism 15 includes a pan axis 21 and a tilt axis 22. The tilt axis 22 is secured against the traveling gantry 14 and parallel with the rotation axis 18 without intersecting with the rotation axis 18. The pan axis 21 is orthogonal with the tilt angle 22. The head swing mechanism 15 rotates the therapeutic radiation irradiation apparatus 16 centering around the pan axis 21 and also rotates the therapeutic radiation irradiation apparatus 16 centering around the tilt axis 22 being controlled by the radiotherapy apparatus control apparatus 2.

The therapeutic radiation irradiation apparatus 16 irradiates therapeutic radiation 23 being controlled by the radiotherapy apparatus control apparatus 2. The therapeutic radiation 23 is irradiated almost along with a straight line passing through an intersection point where the pan axis 21 and the tilt axis 22 are intersected each other. The therapeutic radiation 23 is formed so as to have a uniform intensity distribution. Furthermore, a shape of an irradiation field of the therapeutic radiation 23 is controlled by shielding a part of it when the therapeutic radiation 23 is irradiated to a patient.

As described above, the therapeutic radiation 23 always passes through the isocenter 19 when the therapeutic radiation irradiation apparatus 16 is adjusted by the head swing mechanism 15 once so as to face the isocenter 19 by being supported by the traveling gantry 14, even if the O-ring 12 is rotated by the evolution driving apparatus 11 or the traveling gantry 14 is rotated by its traveling driving apparatus. That is to say, the therapeutic radiation 23 can be irradiated from arbitrary directions to the isocenter 19 by being traveled and rotated.

The radiotherapy apparatus 3 further includes a plurality of imager systems. That is to say, the radiotherapy apparatus 3 includes diagnostic x-ray sources 24 and 25 and sensor arrays 32 and 33. The diagnostic x-ray source 24 is supported on the traveling gantry 14. The diagnostic x-ray source 24 is arranged inside the ring of the traveling gantry 14 and at a position where a line segment connecting the isocenter 19 with the diagnostic x-ray source 24 and a line segment connecting the isocenter 19 with the therapeutic radiation irradiation apparatus 16 make an acute angle. The diagnostic x-ray source 24 irradiates the diagnostic x-ray 35 to the isocenter 19 being controlled by the radiotherapy apparatus control apparatus 2. The diagnostic x-ray 35 is irradiated from one point included in the diagnostic x-ray source 24, and is a conical corn beam formed by including the one point as its apex. The diagnostic x-ray source 25 is supported on the traveling gantry 14. The diagnostic x-ray source 25 is arranged inside the ring of the traveling gantry 14 and at a position where a line segment connecting the isocenter 19 with the diagnostic x-ray source 25 and a line segment connecting the isocenter 19 with the therapeutic radiation irradiation apparatus 16 make an acute angle. The diagnostic x-ray source 25 irradiates the diagnostic x-ray 36 to the isocenter 19 being controlled by the radiotherapy apparatus control apparatus 2. The diagnostic x-ray 36 is irradiated from one point included in the diagnostic x-ray source 25, and is a conical corn beam formed by including the one point as its apex.

The sensor array 32 is supported on the traveling gantry 14. The sensor array 32 receives the diagnostic x-ray 35 which is irradiated from the diagnostic x-ray source 24 and transmits an object around the isocenter 19, and generates a transfer image of the object. The sensor array 33 is supported on the traveling gantry 14. The sensor array 33 receives the diagnostic x-ray 36 which is irradiated from the diagnostic x-ray source 25 and transmits an object around the isocenter 19, and generates a transfer image of the object. An FPD (Flat Panel Detector) and an X-ray II (Image Intensifier) are exemplified as the sensor arrays 32 and 33.

According to such imager system, transfer images centering around the isocenter 19 can be generated based on image signals obtained by the sensor arrays 32 and 33.

The radiotherapy apparatus 3 further includes a sensor array 31. The sensor array 31 is arranged so that a line segment connecting the sensor array 31 with the therapeutic radiation irradiation apparatus 16 can pass the isocenter 19, and secured inside the ring of the traveling gantry 14. The sensor array 31 receives the therapeutic radiation 23 which is irradiated from therapeutic radiation irradiation apparatus 16 and transmits the object around the isocenter 19, and generates a transfer image of the object. An FPD (Flat Panel Detector) and an X-ray II (Image Intensifier) are exemplified as the sensor array 31.

The radiotherapy apparatus 3 further includes a couch 41 and a couch driving apparatus 42. The couch 41 is used for a patient 43 who is to lie thereon to be treated by the radiotherapy system 1. The couch 41 includes retainers not shown in the drawing. The retainers secure the patient on the couch 41 so that the patient cannot move. The couch driving apparatus 42 supports the couch 41 on a base and moves the couch 41 being controlled by the radiotherapy apparatus control apparatus 2.

Figure 3:
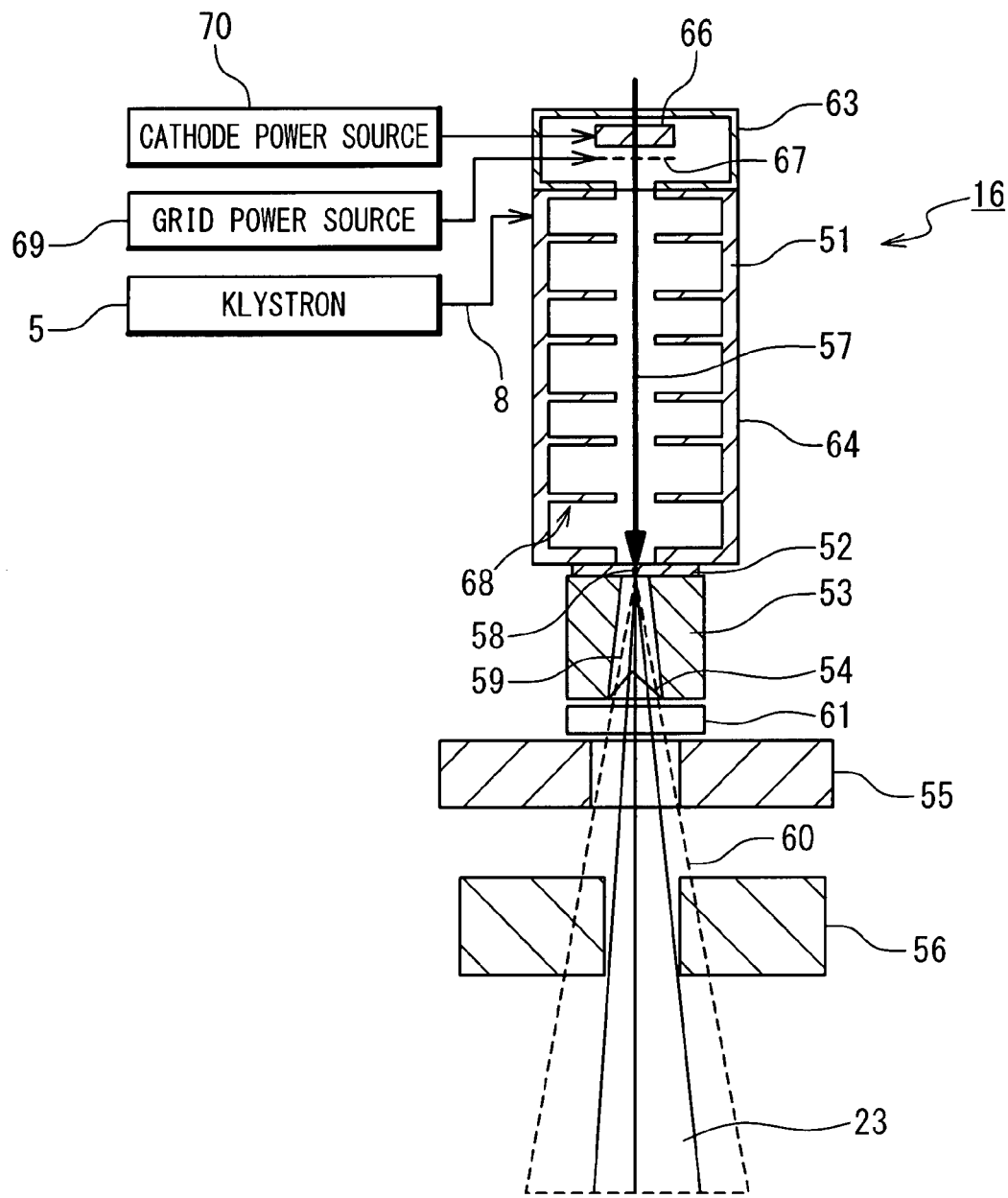
FIG. 3 is a sectional view showing a therapeutic radiation irradiation apparatus in the embodiment.

FIG. 3 shows the therapeutic radiation irradiation apparatus 16. The therapeutic radiation irradiation apparatus 16 includes an electron beam acceleration apparatus 51, an X-ray target 52, a primary collimator 53, a flattening filter 54, a dose meter 61, a secondary collimator 55, and a multi-leaf collimator 56. The electron beam acceleration apparatus 51 emits an electron beam 57 generated by accelerating electrons to the X-ray target 52. The X-ray target 52 is formed of a material with high atomic number (tungsten, tungsten alloy, and the like), and emits a radiation 59 generated by the bremsstrahlung caused by incidence of the electron beam 57. The radiation 59 is irradiated almost along with a straight line passing a virtual point radiation source 58 that the X-ray target 52 includes in its inside. The primary collimator 53 is formed of a material with high atomic number (lead, tungsten, and the like), and shields the radiation 59 so that the radiation 59 cannot be emitted to areas other than a desired area. The flattening filter 54 is formed of aluminum and the like, and formed as a board on which approximately corn-shaped projections are formed. The flattening filter 54 is arranged so that the projections can face the X-ray target side. A shape of the flattening filter 54 is formed so that a dose of the radiation in a predetermined flat area vertical to its irradiation direction can be distributed almost uniformly after passing the flattening filter 54. The secondary collimator 55 is formed of a material with high atomic number (lead, tungsten, and the like), and shields the radiation 60 so that the radiation 60 cannot be emitted to areas other than a desired area. The radiation 60 having uniform intensity distribution, which is formed as described above, is partly shielded by the multi-leaf collimator 56 controlled by the radiotherapy apparatus control apparatus 2, and becomes the therapeutic radiation 23 having a property based on a treatment plan separately prepared. That is to say, the multi-leaf collimator 56 controls a shape of an emission field by shielding a part of the radiation 60 being controlled by the radiotherapy apparatus control apparatus 2 when the therapeutic radiation 23 is irradiated to the patient 23.

The dose meter 61 is a transmission type ionization chamber for measuring intensity of a transmissive radiation, and arranged between the primary collimator 53 and the secondary collimator 55 so that the radiation 60 can transmit. The dose meter 61 measures a dose of the transmissive radiation 60, and outputs the dose to the radiotherapy apparatus control apparatus 2. The dose meter 61 described above is preferable because a nondestructive inspection can be made. In addition, other X-ray intensity detector different from the transmission type ionization chamber can be applied for the dose meter 61. A semiconductor detector and a scintillation detector are exemplified as the X-ray intensity detector. Since being difficult to be alternatively arranged on a radiation path like the transmission type ionization chamber, the semiconductor detector or the scintillation detector is preferably to be arranged outside the path, for example, secured on the traveling gantry 14 so as to be arranged on a position facing the therapeutic radiation irradiation apparatus 16 apart from the isocenter 19. Since generally needing a time constant of a few seconds, the ionization chamber has inferior responsibility. Although having a lower signal intensity than that of the ionization chamber when arranged outside the path, it is preferable since the semiconductor detector or the scintillation detector has better responsibility than the ionization chamber.

The electron beam acceleration apparatus 51 includes an electron beam generation portion 63 and an acceleration tube 64. The electron beam generation portion 63 includes a cathode 66 and a grid 67. The acceleration tube 64 is formed in a cylindrical shape, and includes a plurality of electrodes 68 lining with appropriate interval inside the cylinder. The radiotherapy apparatus 3 further includes a cathode power source 70 and a grid power source 69. The cathode power source 70 supplies electric power for the cathode 66 so that the cathode 66 is heated to emits a predetermined amount of electrons from the cathode 66 (that is, so that a temperature of the cathode 66 can be maintained at predetermined value) being controlled by the radiotherapy apparatus control apparatus 2. The grid 69 applies predetermined voltage between the grid 67 and the cathode 66 so that only a predetermined amount of electrons can be emitted from the electron beam generation portion 63 being controlled by the radiotherapy apparatus control apparatus 2. The klystron 5 is connected to the acceleration tube 64 via the waveguide 8. The klystron 5 emits a microwave into the acceleration tube 64 via the waveguide 8 so that the acceleration tube 64 can accelerate electrons emitted from the electron beam generation portion 63 to let the electrons have predetermined energy being controlled by the radiotherapy apparatus control apparatus 2.

Figure 4:
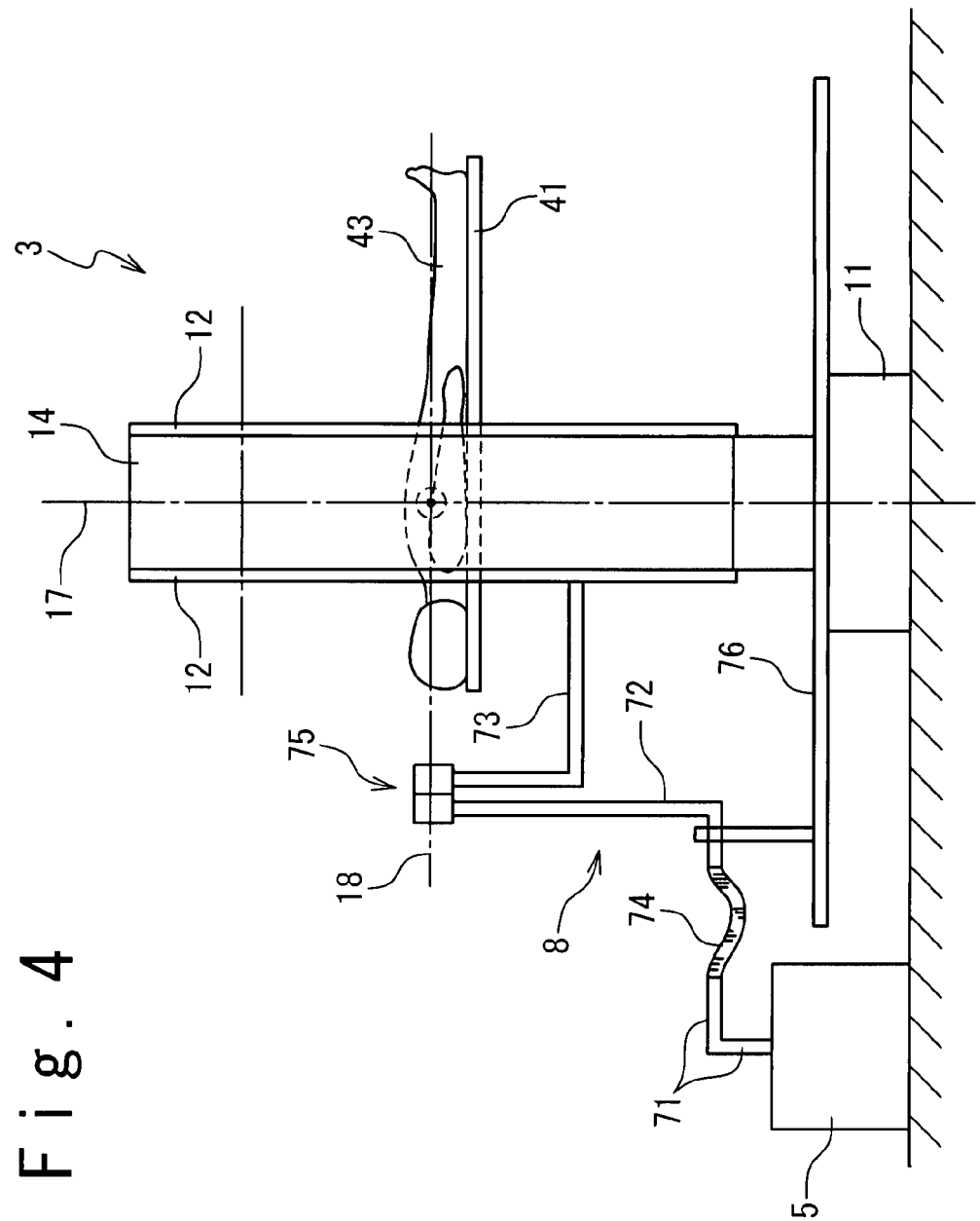
FIG. 4 is a side view showing a waveguide in the embodiment.

As shown in FIG. 4, the klystron 5 is supported on a base on which the radiotherapy apparatus 3 is supported. The waveguide 8 forms a waveguide in which high frequency waves generated by the klystron 5 transmit. The waveguide 8 includes secured waveguide 71, 72, and 73, a flexible waveguide 74, and a rotary joint 75. The secured waveguide 71 forms a waveguide which cannot be transformed, which is supported on the base, and is connected to the klystron 5 at one end thereof. The secured waveguide 72 forms a waveguide which cannot be transformed, and is supported by a turntable 76. A turntable 76 is rotatably supported by the evolution driving apparatus 11 centering around the rotation axis 17, and rotates being integrated with the O-ring 12 centering around the rotation axis 17. As a result, the secured waveguide 72 rotates being integrated with the O-ring 12 centering around the rotation axis 17. The secured waveguide 73 forms a waveguide which cannot be transformed, which is supported on the traveling gantry 14 and moves being integrated with the traveling gantry 14.

The flexible waveguide 74 is formed in a bellows structure and forms a bendable and stretchable waveguide. The flexible waveguide 74 is connected to the secured waveguide 71 at one end thereof and to the secured waveguide 72 at the other end thereof. The flexible waveguide 74 is transformed by a rotation of the O-ring 12 against the base and a shape of the flexible waveguide 74 approximately corresponds to an evolution angle of the O-ring 12 against the base. That is to say, the evolution angle of the rotation of the O-ring 12 centering around the rotation axis 17 against the base is restricted by a range in which the flexible waveguide 74 can be transformed.

The rotary joint 75 forms a transformable waveguide, and is arranged so as to overlap with the rotation axis 18. The rotary joint 75 is connected to the secured waveguide 72 at one end thereof and to the secured waveguide 73 at the other end thereof.

Figure 5:
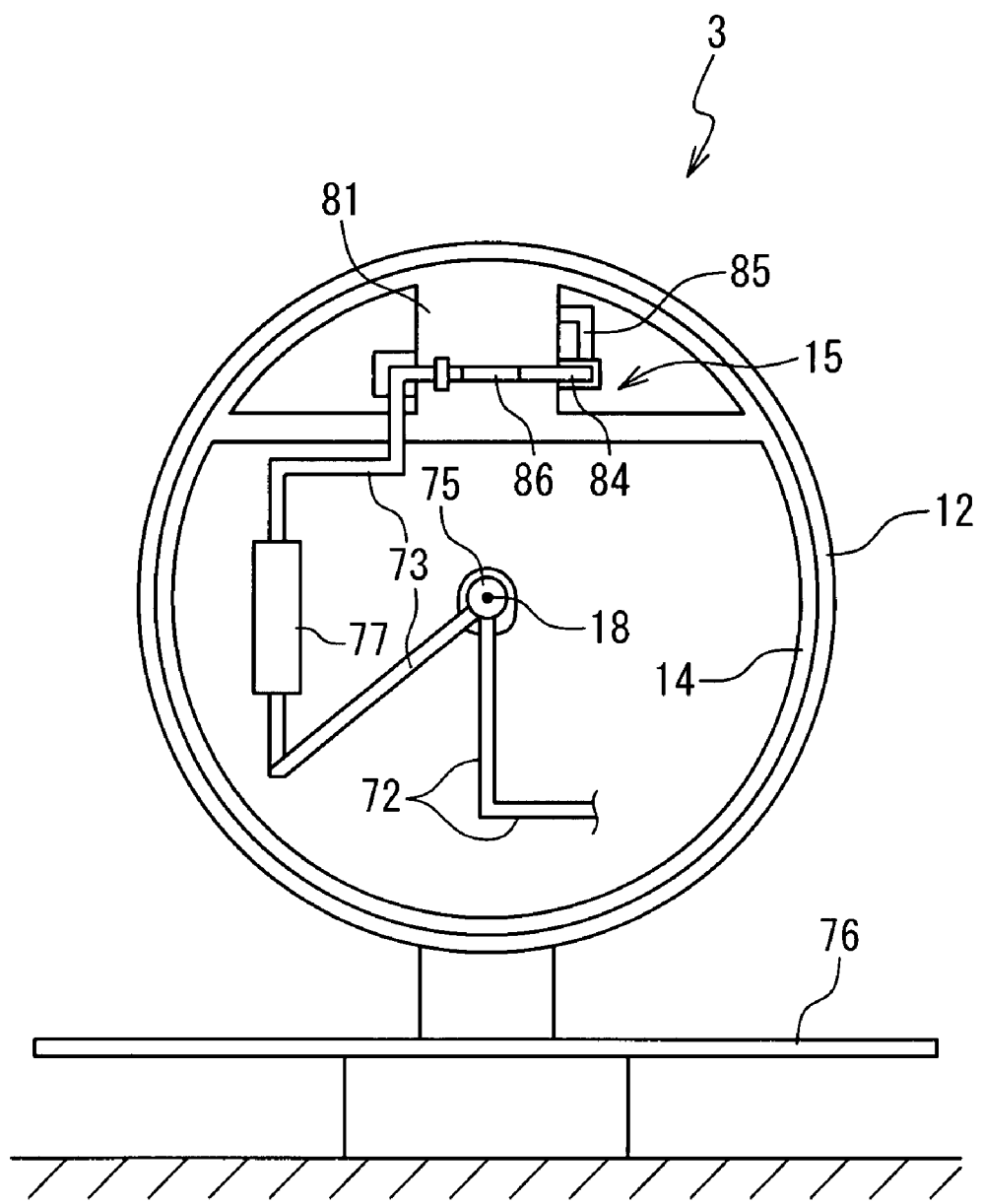
FIG. 5 is an elevation view showing the waveguide in the embodiment.

As shown in FIG. 5, in the secured waveguide 73, an end opposite to the end connected to the rotary joint 75 is arranged in the vicinity of the head swing mechanism 15. As shown in FIG. 5, the waveguide 8 further includes a circulator 77. The circulator 77 is a non-reciprocal circuit element and arranged in the middle of the secured waveguide 73. The circulator 77 attenuates a reflecting wave traveling from the acceleration tube 64 to the klystron 5 compared to a high frequency wave traveling from the klystron 5 to the acceleration tube 64 in the secured waveguide 73.

A part of the microwave emitted into the acceleration tube 64 is reflected. This reflectance ratio is constant based on a degree of resonance of the acceleration tube 64. In a free waveguide such as the rotary joint 75, a part of the microwave is reflected. Thus, a part of the wave reflected from the acceleration tube 64 goes to the acceleration tube 64 after being reflected at the rotary joint 75 again. However, since the wave reflected from the acceleration tube 64 can be arranged outside the system because of an arrangement of the circulator 77, negation and distortion caused by superimposing of the microwave supplied from the klystron 5 on the reflected microwave can be suppressed as a result.

Figure 6:
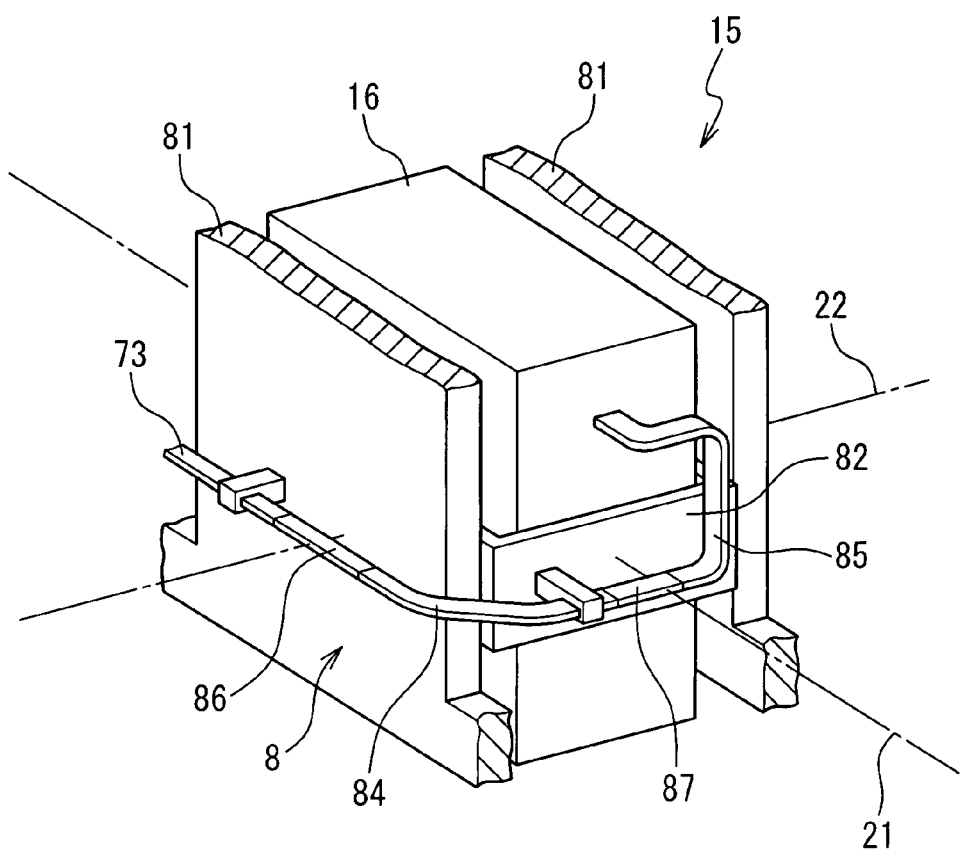
FIG. 6 is a perspective view showing a head swing mechanism and the waveguide in the embodiment.

FIG. 6 shows the head swing mechanism 15. The head swing mechanism 15 includes an irradiation apparatus support member 81 and an intermediate member 82. The irradiation apparatus support member 81 is supported by the traveling gantry 14, and moves being integrated with the traveling gantry 14. The tilt axis 22 is secured against the irradiation apparatus support member 81. The intermediate member 82 is supported by the irradiation apparatus support member 81 rotatably centering around the tilt axis 22. The pan axis 21 is secured against the intermediate member 82. The therapeutic radiation irradiation apparatus 16 is supported by the intermediate member 82 rotatably centering around the pan axis 21. In addition, since the head swing mechanism 15 is used for adjusting the therapeutic radiation 23 to face the isocenter 19, it is preferable for the pan axis 21 and the tilt axis 22 to be arranged so that an intersection point of them approximately agree with the virtual point radiation source 58.

The head swing mechanism 15 further includes a pan axis driving apparatus and a tilt axis driving apparatus not shown in the drawing. The pan axis driving apparatus rotates the therapeutic radiation irradiation apparatus 16 centering around the pan axis 21 being controlled by the radiotherapy apparatus control apparatus 2. The tilt axis driving apparatus rotates the intermediate member 82 centering around the tilt axis 22 being controlled by the radiotherapy apparatus control apparatus 2.

The waveguide 8 further includes a secured waveguide 84, a secured waveguide 85, a flexible waveguide 86, and a flexible waveguide 87. The secured waveguide 84 forms a waveguide which cannot be transformed, is supported on the intermediate member 82, and moves being integrated with the intermediate member 82. The secured waveguide 85 forms a waveguide which cannot be transformed, is supported on the therapeutic radiation irradiation apparatus 16, and moves being integrated with the therapeutic radiation irradiation apparatus 16. The secured waveguide 85 is connected to the acceleration tube 64 at one end thereof. The flexible waveguide 86 and the flexible waveguide 87 are formed in a bellows structure and form bendable and stretchable waveguides. The flexible waveguide 86 is arranged so as to overlap the tilt axis 22, is connected to the secured waveguide 73 at one end thereof, and is connected to the secured waveguide 84 at the other end thereof. The flexible waveguide 86 is transformed by a rotation of the therapeutic radiation irradiation apparatus 16 against the intermediate member 82 and a shape of the flexible waveguide 86 approximately corresponds to a tilt angle of the therapeutic radiation irradiation apparatus 16 against the intermediate member 82. The flexible waveguide 87 is arranged so as to overlap the pan axis 21, is connected to the secured waveguide 84 at one end thereof, and is connected to the secured waveguide 85 at the other end thereof. The flexible waveguide 87 is transformed by a rotation of the intermediate member 82 against the irradiation apparatus support member 81 and a shape of the flexible waveguide 87 approximately corresponds to a pan angle of the intermediate member 82 against the irradiation apparatus support member 81.

Figure 7:
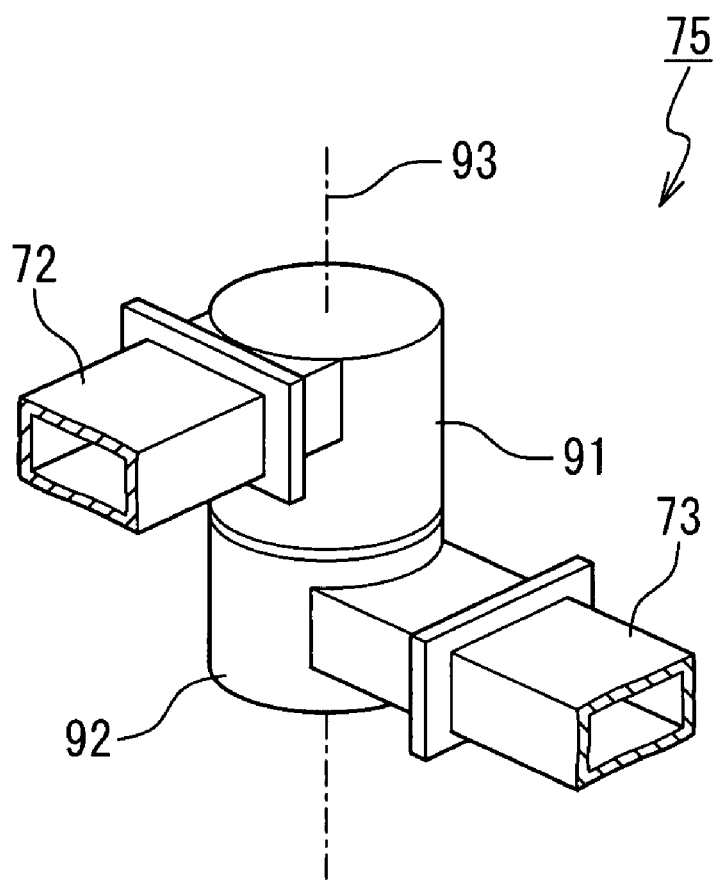
FIG. 7 is a perspective view showing a rotary joint in the embodiment.

FIG. 7 shows the rotary joint 75. The rotary joint 75 includes a first cylinder portion 91 and a second cylinder portion 92. The first cylinder portion 91 is formed in a cylindrical shape centering around the rotation axis 93. The second cylinder portion 92 is formed in a cylindrical shape centering around the rotation axis 93, and is supported by the first cylinder portion 91 rotatably centering around the rotation axis 93. The first cylinder portion 91 is connected to one end of the secured waveguide 72 at a part of a side surface of the cylinder. The second cylinder portion 92 is connected to one end of the secured waveguide 73 at a part of a side surface of the cylinder. The rotary joint 75 is arranged on the radiotherapy apparatus 3 so that the rotation axis 93 can overlap the rotation axis 18. That is to say, in the rotary joint 75, the second cylinder portion 92 rotates against the first cylinder portion 91 by rotation of the traveling gantry 14 against the O-ring 12. At this moment, an angle of the second cylinder portion 92 against the first cylinder portion 91 corresponds to a traveling angle of the traveling gantry 14 against the O-ring 12.

The rotary joint 75 connects the secured waveguide 72 with the secured waveguide 73 rotatably so as to transmit a high frequency wave between the secured waveguide 72 and the secured waveguide 73. The rotary joint 75 described above is commonly known, for example, disclosed in Japanese Laid-Open Patent Application JP-P 2005-033463 A.

The evolution angle sensor 6-1 measures a rotation angle which is made by a rotation of the O-ring 12 centering around the rotation axis 17 against a base, and outputs the rotation angle to the control apparatus 7. The traveling angle sensor 6-2 measures a rotation angle which is made by a rotation of the second cylinder portion 92 centering around the rotation axis 93 against the first cylinder portion 91, and outputs the rotation angle to the control apparatus 7. The pan angle sensor 6-3 measures a rotation angle which is made by a rotation of the therapeutic radiation irradiation apparatus 16 centering around the pan axis 21 against the intermediate member 82, and outputs the rotation angle to the control apparatus 7. The tilt angle sensor 6-4 measures a rotation angle which is made by a rotation of the intermediate member 82 centering around the tilt axis 22 against the irradiation apparatus support member 81, and outputs the rotation angle to the control apparatus 7. The transmission efficiency sensor 6-5 is arranged in the vicinity of the acceleration tube 64 in the waveguide 8, for example, in the middle of the secured waveguide 85, measures a progressing high frequency power and a reflected high-frequency power transmitted through the waveguide 8, and calculates a transmission efficiency in which the waveguide 8 transmits the high frequency wave based on the measured of progressing high-frequency power and reflected high-frequency power. The transmission efficiency sensor 6-5 is commonly known, for example, the sensor having a directional coupler is exemplified.

In addition, if a degree of resonance of the acceleration tube 64 can be deemed as a constant value, a physical value corresponding to the transmission efficiency in which the waveguide 8 transmits the high frequency wave can be indirectly evaluated when the transmission efficiency sensor 6-5 measures only the progressing high-frequency power transmitted through the waveguide 8.

Figure 8:
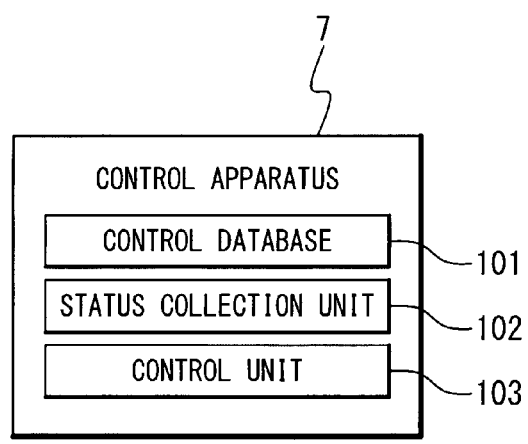
FIG. 8 is a block diagram showing a control apparatus in the embodiment.

FIG. 8 shows the control apparatus 7. The control apparatus 7 is a computer, and includes a CPU, a storage apparatus, an input apparatus, an output apparatus, and an interface, which are not shown in the drawing. The CPU executes computer programs installed in the control apparatus 7 to control the storage apparatus, the input apparatus, the output apparatus, and the interface. The storage apparatus records the computer programs, records information used by the CPU, and records information created by the CPU. The input apparatus outputs information created by user's operation to the CPU. A key board and a mouse are exemplified as the input apparatus. The output apparatus outputs information produced by the CPU to a user in a visible status. A display for displaying a screen created by the CPU is exemplified as the output apparatus. The interface outputs information created by an external apparatus connected to the control apparatus 7 to the CPU, and outputs information created by the CPU to the external apparatus. The external apparatus includes the klystron 5 and the sensor 6.

The control apparatus 7 includes a control database 101, a status collection unit 102 and a control unit 103 which are computer programs.

The control database 101 records a control table showing relation between a measurement value measured by the sensor 6 and a control value for controlling the klystron 5 into the storage apparatus, which is able to be searched and extracted by other computer programs. The control table will be described later.

The status collection unit 102 collects the measurement values measured by the sensor 6 from the sensor 6. That is to say, the status collection unit 102 collects an evolution angle made by a rotation of the O-ring 12 centering around the rotation axis 17 against the base from the evolution angle sensor 6-1. The status collection unit 102 further collects a traveling angle made by a rotation of the second cylinder portion 92 centering around the rotation axis 93 against the first cylinder portion 91 from the traveling angle sensor 6-2. The status collection unit 102 further collects a pan angle made by a rotation of the therapeutic radiation irradiation apparatus 16 centering around the pan axis 21 against the intermediate member 82 from the pan angle sensor 6-3. The status collection unit 102 further collects a tilt angle made by a rotation of the intermediate member 82 centering around the tilt axis 22 against the irradiation apparatus support member 81 from the tilt angle sensor 6-4. The status collection unit 102 further collects a progressing high-frequency power and a reflected high-frequency power transmitted through the waveguide 8 from the transmission efficiency sensor 6-5.

The control unit 103 controls the klystron 5 based on the measuring value collected by the status collection unit 102 referring to the control table recorded by the control database 101.

Figure 9:
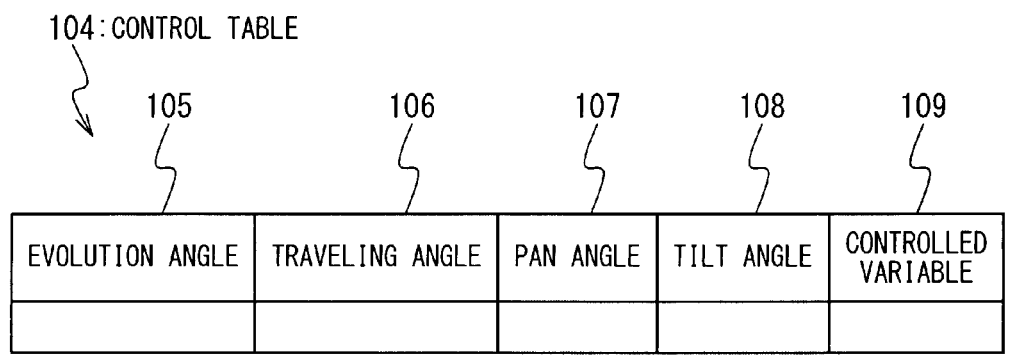
FIG. 9 is a view showing a control table in the embodiment.

FIG. 9 shows the control table recorded by the control database 101. The control table 104 relates an evolution angle 105, a traveling angle 106, a pan angle 107, and a tilt angle 108 to a controlled variable 109. That is to say, a combination of an arbitrary element of the evolution angle 105, an arbitrary element of the traveling angle 106, an arbitrary element of the pan angle 107, and an arbitrary element of the tilt angle 108 corresponds to one element of the controlled variable 109. The evolution angle 105 shows a shape of the flexible waveguide 74, and shows a rotation angle made by a rotation of the O-ring 12 centering around the rotation axis 17 against the base. The traveling angle 106 shows a shape of the rotary joint 75, and shows a rotation angle made by a rotation of the second cylinder portion 92 centering around the rotation axis 93 against the first cylinder portion 91. The pan angle 107 shows a shape of the flexible waveguide 87, and shows a rotation angle made by a rotation of the therapeutic radiation irradiation apparatus 16 centering around the pan axis 21 against the intermediate member 82. The tilt angle 108 shows a shape of the flexible waveguide 86, and shows a rotation angle made by a rotation of the intermediate member 82 centering around the tilt axis 22 against the irradiation apparatus support member 81. The controlled variable 109 shows the controlled variable used for controlling the klystron 5 when the evolution angle, the traveling angle, the pan angle, and the tilt angle are measured by the sensor 6, and shows the oscillation RF intensity, the klystron acceleration voltage, or the klystron electric current.

At this moment, the control unit 103 calculates the controlled variable corresponding to the combination of the evolution angle, the traveling angle, the pan angle, and the tilt angle collected by the status collection unit 102 referring to the control table 104, and controls the klystron 5 so that the oscillation RF intensity of the klystron 5, the klystron acceleration voltage, or the klystron electric current can meet the oscillation RF intensity, the klystron acceleration voltage, or the klystron electric current which are shown by the controlled variable, respectively. The control unit 103 further executes feedback control of the oscillation RF intensity, the klystron acceleration voltage, or the klystron electric current so that predetermined high-frequency power can be supplied for the acceleration tube 64 based on the progressing high-frequency power and a reflected high-frequency power collected by the status collection unit 102.

That is to say, the control table 104 is created so that a constant high-frequency power can be supplied for the acceleration tube 64 when the control apparatus 7 controls the klystron 5 based on the controlled variable corresponding to the combination of the evolution angle, the traveling angle, the pan angle, and the tilt angle collected by the status collection unit 102.

In a radiotherapy using the radiotherapy system 1, a user creates a treatment plan using the radiotherapy apparatus control apparatus 2 at first. The treatment plan shows an irradiation angle at which the therapeutic radiation 23 is irradiated to an affected area of the patient 43, and a dose and a property of the therapeutic radiation 23 irradiated from the respective irradiation angles. The radiotherapy apparatus control apparatus 2 executes a tracking operation and an irradiation operation repeatedly. In the tracking operation, the radiotherapy apparatus control apparatus 2 calculates a position of the affected area based on an image taken by the imager system of the radiotherapy apparatus 3. The calculation of the position of the affected area may be based on a position of a landmark different from the affected area. An internal organ and an object moving in conjunction with the affected area are exemplified as the landmark. A bone (rib), a diaphragm, and a bladder are exemplified as the internal organ. The object is formed of a material able to be detected by the imager system, and is embedded in the body of the patient so as to move in conjunction with the affected area. A gold marker which is a ball made of gold is exemplified as the object. The radiotherapy apparatus control apparatus 2 moves the therapeutic radiation irradiation apparatus 16 using the head swing mechanism 15 so that the therapeutic radiation 23 can transmit the position of the affected area. In the irradiation operation, the radiotherapy apparatus control apparatus 2 irradiates the therapeutic radiation 23 to the affected area using the therapeutic radiation irradiation apparatus 16 immediately after the therapeutic radiation irradiation apparatus 16 moved by the tracking operation.

The control apparatus 7 operates in parallel with the irradiation operation. The control apparatus 7 collects the evolution angle made by the rotation of the O-ring 12 centering around the rotation axis 17 against the base from the evolution angle sensor 6-1 at first. The control apparatus 7 further collects the traveling angle made by the rotation of the second cylinder portion 92 centering around the rotation axis 93 against the first cylinder portion 91 from the traveling angle sensor 6-2. The control apparatus 7 further collects a pan angle made by a rotation of the therapeutic radiation irradiation apparatus 16 centering around the pan axis 21 against the intermediate member 82 from the pan angle sensor 6-3. The control apparatus 7 further collects a tilt angle made by a rotation of the intermediate member 82 centering around the tilt axis 22 against the irradiation apparatus support member 81 from the tilt angle sensor 6-4. The control apparatus 7 further collects the progressing high-frequency power and the reflected high-frequency power transmitted through the waveguide 8 from the transmission efficiency sensor 6-5.

The control apparatus 7 calculates the controlled variable corresponding to the combination of the evolution angle, the traveling angle, the pan angle, and the tilt angle measured by the sensor 6 referring to the control table 104. The control apparatus 7 controls the klystron 5 so that the oscillation RF intensity, the klystron acceleration voltage, or the klystron electric current can meet the oscillation RF intensity, the klystron acceleration voltage, or the klystron electric current which are shown by the controlled variable, respectively. The control apparatus 7 further executes feedback control of the oscillation RF intensity, the klystron acceleration voltage, or the klystron electric current so that predetermined high-frequency power can be supplied for the acceleration tube 64 based on the progressing high-frequency power and a reflected high-frequency power measured by the transmission efficiency sensor 6-5. The control apparatus 7 executes these operations periodically and repeatedly.

Figure 10:
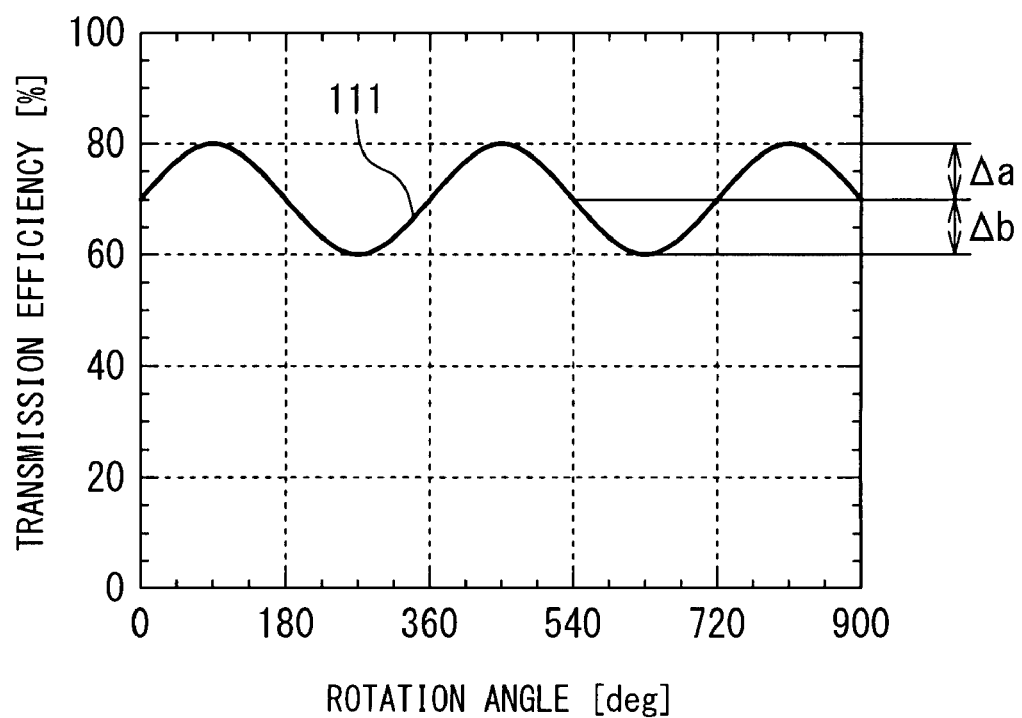
FIG. 10 is a graph showing a relation between a rotation angle of the rotary joint and a transmission efficiency of high frequency wave in the embodiment.

FIG. 10 shows a relation between a rotation angle of the second cylinder portion 92 against the first cylinder portion 91 of the rotary joint 75 and the transmission efficiency of the high frequency wave. The relation 111 shows that a transmission efficiency corresponding to a rotation angle θ is equal to a transmission efficiency corresponding to a rotation angle θ+2πn by using an arbitrary integer number n. The relation 111 also shows that there is a case where a transmission efficiency corresponding to a rotation angle θ+2πn is different from a transmission efficiency corresponding to other different rotation angle θ' (θ' is not equal to θ+2πn). That is to say, the relation 111 shows that the transmission efficiency changes depending on rotations of the first cylinder portion 91 and the second cylinder portion 92 of the rotary joint 75. In addition, an absolute value of the changing volume is not limited to the same even in opposite phase, and generally Aa and Ab are different from each other. Although these changing of the transmission efficiency cannot occur in theory, it can practically occur when the rotary joint 75 is rotated. One reason is that a part of the rotary joint 75 (for example, a space between the first cylinder portion 91 and the second cylinder portion 92) is changed because of a mechanical precision and an assembly accuracy of constituent elements. Another reason is that a coupling coefficient between both cylindrical parts is changed because of the mechanical precision and the assembly accuracy of the constituent elements.

In addition, regarding the flexible waveguides 74, 86, and 87, the transmission efficiency also changes similarly to the rotary joint 75 depending on its transformation. That is to say, the flexible waveguide 74 changes its transmission efficiency by rotating of the O-ring 12 centering around the rotation axis 17 against the base, and the transmission efficiency corresponds to the evolution angle. The flexible waveguide 86 changes its transmission efficiency by rotating of the intermediate member 82 centering around the tilt axis 22 against the irradiation apparatus support member 81, and the transmission efficiency corresponds to the tilt angle. The flexible waveguide 87 changes its transmission efficiency by rotating of the therapeutic radiation irradiation apparatus 16 centering around the pan axis 21 against the intermediate member 82, and the transmission efficiency corresponds to the pan angle.

Figure 11:
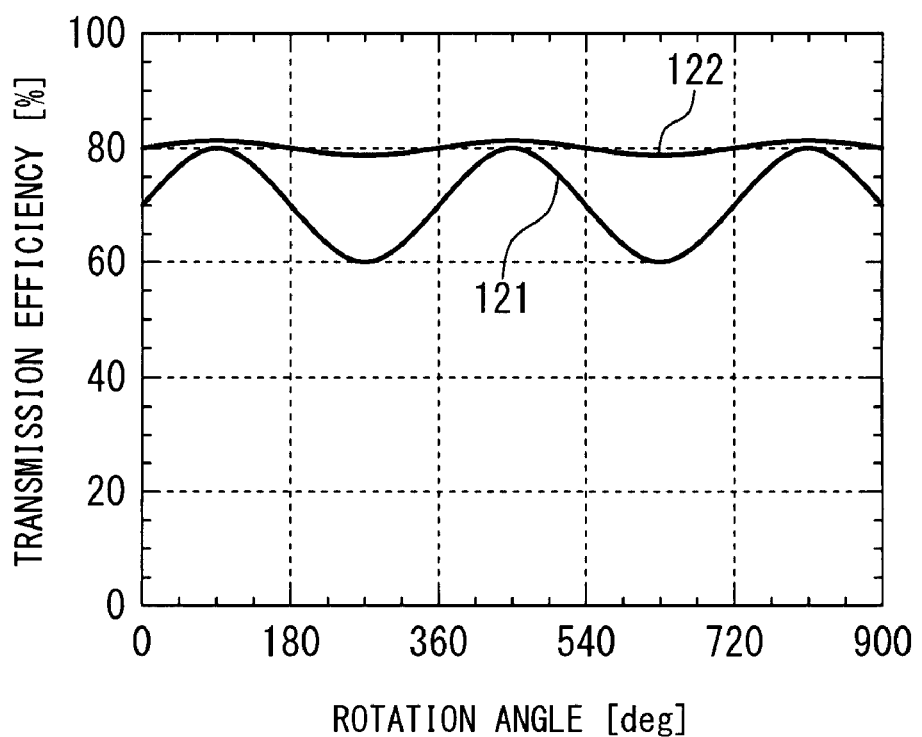
FIG. 11 is a graph showing a relation between the rotation angle of the rotary joint and the transmission efficiency of high frequency wave when the waveguide tube does not include a circulator, and showing a relation between the rotation angle of the rotary joint and the transmission efficiency of high frequency wave when the waveguide tube includes a circulator in the embodiment.

FIG. 11 shows a relation between the rotation angle of the second cylinder portion 92 against the first cylinder portion 91 of the rotary joint 75 and the transmission efficiency of the high frequency wave when the waveguide 8 does not include the circulator 77. The transmission efficiency is measured in an area closer to the acceleration tube 64 (for example, in the middle of the secured waveguide 85) than the free waveguides (the flexible waveguides 74, 86, and 87, and the rotary joint 75) in the waveguide 8. The relation 121 shows that a transmission efficiency corresponding to a rotation angle θ is equal to a transmission efficiency corresponding to a rotation angle θ+2πn. The relation 121 also shows that there is a case where a transmission efficiency corresponding to a rotation angle θ+2πn is different from a transmission efficiency corresponding to other different rotation angle θ' (θ' is not equal to θ+2πn) That is to say, a relation 121 shows that the transmission efficiency changes depending on rotations of the first cylinder portion 91 and the second cylinder portion 92 of the rotary joint 75. Although these changing of the transmission efficiency cannot occur in theory, it can practically occur when the rotary joint 75 is rotated. One reason is that a part of the rotary joint 75 (for example, a space between the first cylinder portion 91 and the second cylinder portion 92) is changed because of a machine precision and an assembly accuracy of constituent elements. Another reason is that a coupling coefficient between both cylindrical parts is changed because of the machine precision and the assembly accuracy of the constituent elements.

FIG. 11 further shows a relation between the rotation angle of the second cylinder portion 92 against the first cylinder portion 91 of the rotary joint 75 and the transmission efficiency of the high frequency wave when the waveguide 8 includes the circulator 77. The relation 122 shows that a transmission efficiency corresponding to a rotation angle θ is equal to a transmission efficiency corresponding to a rotation angle θ+2πn. The relation 122 also shows that there is a case where a transmission efficiency corresponding to a rotation angle θ+2πn is different from a transmission efficiency corresponding to other different rotation angle θ' (θ' is not equal to θ+2πn). The relation 122 further shows that a magnitude of the changing of the transmission efficiency is smaller than that of the transmission efficiency shown by the relation 121. That is to say, FIG. 11 shows that the magnitude of the changing of the transmission efficiency of the high frequency wave transmitted from the waveguide 8 can be reduced when the waveguide 8 includes the circulator 77.

Figure 12:
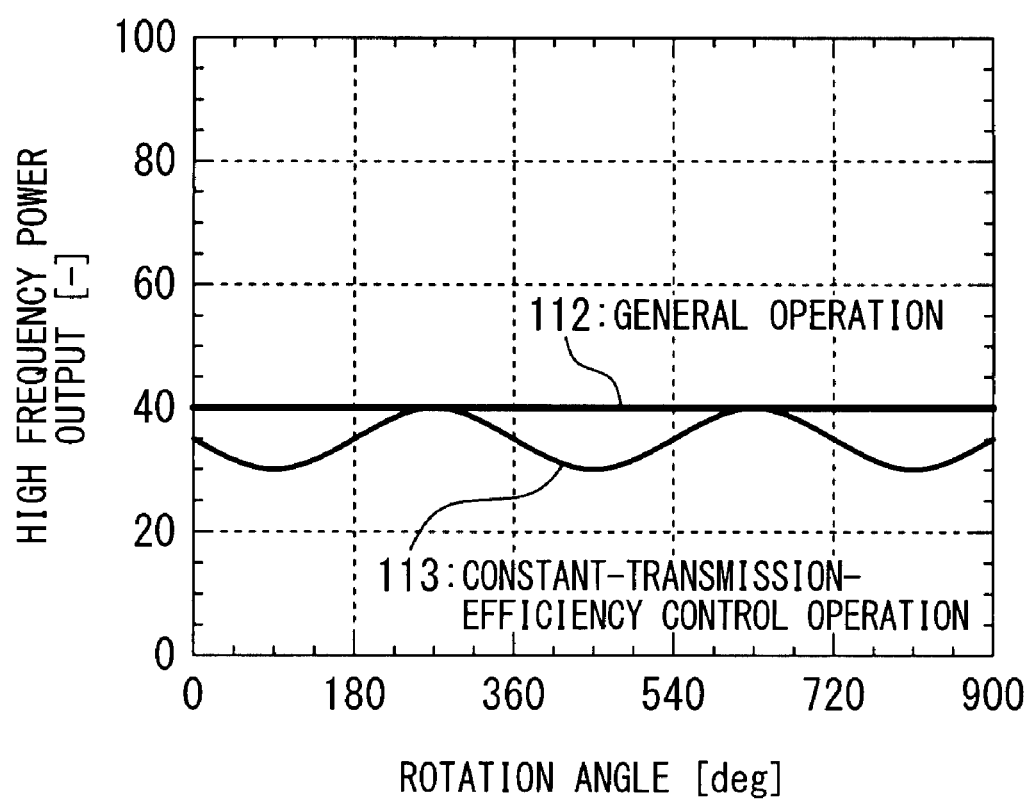
FIG. 12 is a graph showing a relation between the rotation angle of the rotary joint and a high-frequency power outputted from a klystron in the embodiment.

FIG. 12 shows a relation between a rotation angle of the rotary joint 75 and the high-frequency power outputted from the klystron 5 in a case where the control apparatus 7 does not control the klystron 5 based on the measurement value of the sensor 6. The relation 112 shows that the high-frequency power is independent from the rotation angle, and that the high-frequency power is constant (general operation). FIG. 12 further shows a relation between the rotation angle of the rotary joint 75 and the high-frequency power outputted from the klystron 5 in a case where the control apparatus 7 controls the klystron 5 based on the measurement value of the sensor 6 if the flexible waveguide tubes 74, 86, and 87 are not transformed. The relation 113 shows that the high-frequency power corresponds to the rotation angle (constant-transmission-efficiency control operation). The relation 113 also shows that the high-frequency power corresponding to a rotation angle $\theta$ is equal to the high-frequency power corresponding to a rotation angle $\theta+2\pi n$. That is to say, the control apparatus 7 controls the klystron 5 so that the high-frequency power can correspond to the rotation angle, and the high-frequency power corresponding to the rotation angle $\theta$ can correspond to the rotation angle $\theta+2\pi n$.

Figure 13:
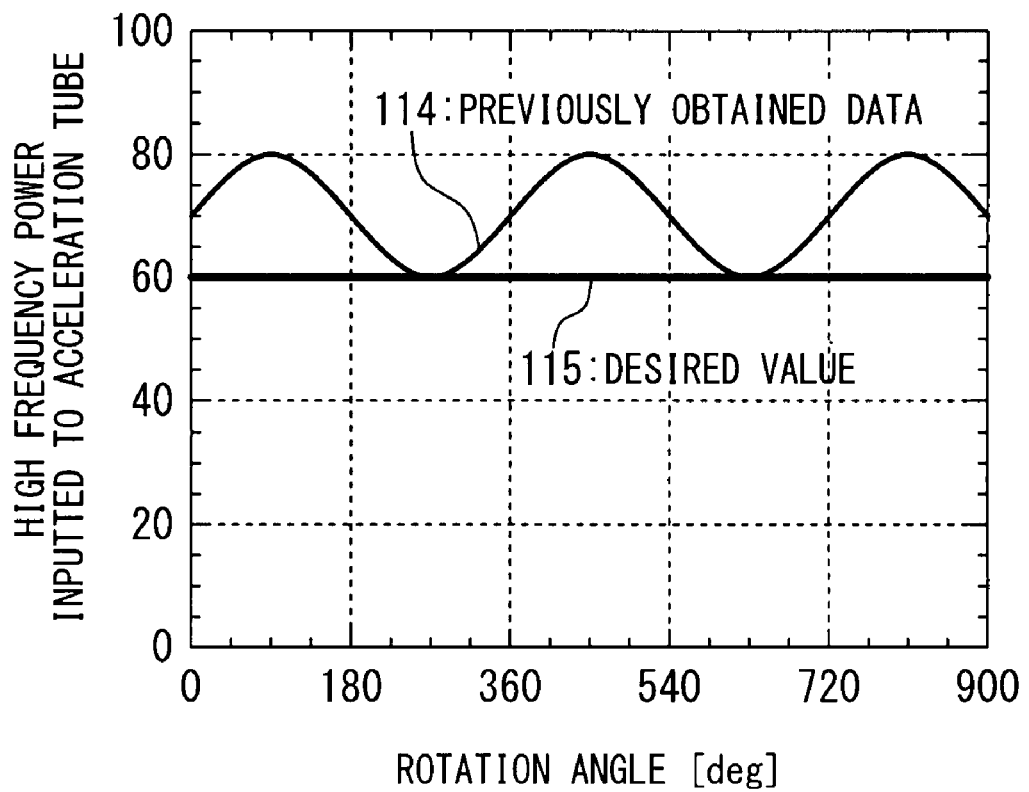
FIG. 13 is a graph showing a relation between the rotation angle of the rotary joint and a high-frequency power supplied to an acceleration tube in the embodiment.

FIG. 13 shows a relation between the rotation angle of the rotary joint 75 and the high-frequency power inputted to the acceleration tube 64 in a case where the klystron 5 outputs the high frequency wave as shown in the relation 112. The relation 114 shows that a transmission efficiency corresponding to a rotation angle $\theta$ is equal to a transmission efficiency corresponding to a rotation angle $\theta+2\pi n$ (previously obtained data). The relation 114 also shows that there is a case where a transmission efficiency corresponding to a rotation angle $\theta+2\pi n$ is different from a transmission efficiency corresponding to other different rotation angle $\theta'$ ($\theta'$ is not equal to $\theta+2\pi n$). FIG. 13 further shows a relation between the rotation angle of the rotary joint 75 and the high-frequency power inputted to the acceleration tube 64 in a case where the klystron 5 outputs the high frequency wave as shown in the relation 113. The relation 115 shows that the high-frequency power is independent from the rotation angle, and that the high-frequency power is constant (desired value).

The radiotherapy system 1 according to the present invention is able to supply high frequency wave having small changing of the high-frequency power for the acceleration tube 64 even when the acceleration tube 64 moves against the klystron 5, able to reduce the changing of the energy of the electron beam 57 generated by the acceleration tube 64, and able to reduce the changing of the energy (energy distribution) and intensity of the therapeutic radiation 23. As a result, the radiotherapy system 1 according to the present invention is able to control the dose of the therapeutic radiation 23 with higher precision.

In another embodiment of the radiotherapy system according to the present invention, the status collection unit 102 in the embodiments described above is replaced by another status collection unit (not shown). The status collection unit collects status control signals from the radiotherapy apparatus control apparatus 2. Here, the status control signals are transmitted from the radiotherapy apparatus control apparatus 2 to the evolution driving apparatus 11, the traveling driving apparatus, the pan axis driving apparatus, and the tilt axis driving apparatus, respectively. Then, the status collection unit calculates the status of the waveguide 8 based on the collected control signals. That is to say, the status collection unit calculates the evolution angle made by the rotation of the O-ring 12 centering around the rotation axis 17 against the base based on the status control signals. The status collection unit further calculates the traveling angle made by the rotation of the second cylinder portion 92 centering around the rotation axis 93 against the first cylinder portion 91 based on the status control signals. The status collection unit further calculates the pan angle made by the rotation of the therapeutic radiation irradiation apparatus 16 centering around the pan axis 21 against the intermediate member 82 based on the status control signals. The status collection unit further calculates the tilt angle made by the rotation of the intermediate member 82 centering around the tilt axis 22 against the irradiation apparatus support member 81 based on the status control signals. The status collection unit further collects the progressing high-frequency power and the electric power of reflected high-frequency power transmitted by the waveguide 8 from the transmission efficiency sensor 6-5.

Similar to the radiotherapy system 1, such radiotherapy system is able to supply high frequency wave having small changing of the high-frequency power for the acceleration tube 64, able to reduce the changing of the energy of the electron beam 57 generated by the acceleration tube 64, and able to reduce the changing of the energy (energy distribution) and intensity of the therapeutic radiation 23. Such radiotherapy system can be manufactured in low cost since the evolution angle sensor 6-1, the traveling angle sensor 6-2, the pan angle sensor 6-3, and the tilt angle sensor 6-4 are not required to be provided.

In further another embodiment of the radiotherapy system according to the present invention, the control unit 103 in the embodiments described above is replaced by another control unit (not shown). The control unit calculates the controlled variable corresponding to the combination of the evolution angle, the traveling angle, the pan angle, and the tilt angle collected by the status collection unit 102 referring to the control table 104, and controls the klystron 5 so that the oscillation RF intensity, the klystron acceleration voltage, or the klystron electric current can meet the oscillation RF intensity, the klystron acceleration voltage, or the klystron electric current which are shown by the controlled variable, respectively.

Similar to the radiotherapy system 1, such radiotherapy system is able to supply high frequency wave having small changing of the high-frequency power for the acceleration tube 64, able to reduce the changing of the energy of the electron beam 57 generated by the acceleration tube 64, and able to reduce the changing of the energy (energy distribution) and intensity of the therapeutic radiation 23. Such radiotherapy system can be manufactured in low cost since the transmission efficiency sensor 6-5 is not required to be provided.

In further another embodiment of the radiotherapy system according to the present invention, the control unit 103 in the embodiments described above is replaced by another control unit (not shown). The control unit executes feedback control of the oscillation RF intensity, the klystron acceleration voltage, or the klystron electric current so that predetermined high-frequency power can be supplied for the acceleration tube 64 based on the progressing high-frequency power and a reflected high-frequency power collected by the status collection unit 102.

Although, such radiotherapy system delays a response compared to the radiotherapy system 1 since an initial value used in the feedback control is not determined based on the shape of the waveguide formed by the waveguide 8, similar to the radiotherapy system 1, such radiotherapy system is able to supply high frequency wave having small changing of the high-frequency power for the acceleration tube 64, able to reduce the changing of the energy of the electron beam 57 generated by the acceleration tube 64, and able to reduce the changing of the energy (energy distribution) and intensity of the therapeutic radiation 23.

In addition, the klystron 5 can be replaced by another high frequency wave source (not shown). A magnetron and a multielectrode tube are exemplified as the high frequency wave source. The magnetron generates high frequency wave in predetermined high-frequency power by controlling a magnetron current. At this moment, the control apparatus 7 is able to reduce changing of the energy of the electron beam 57 by controlling the magnetron current, and reduce changing of the energy (energy distribution) and intensity of the therapeutic radiation 23. The multielectrode tube generates high frequency wave in predetermined high-frequency power by controlling the oscillation RF intensity, a multielectrode tube acceleration voltage, or a multielectrode tube current. At this moment, the control apparatus 7 is able to reduce the changing of the energy of the electron beam 57 generated by the acceleration tube 64, and able to reduce the changing of the energy (energy distribution) and intensity of the therapeutic radiation 23 by controlling the oscillation RF intensity, the multielectrode tube acceleration voltage, or the multielectrode tube current.

In addition, the control table 104 is able to further relate a combination of other status different from the shape of the waveguide according to the waveguide 8 to the controlled variable 109. Temperatures of respective parts of the waveguide 8 are exemplified as the status. At this moment, superior to the radiotherapy system 1, the control apparatus 7 is able to supply high frequency wave having small changing of the high-frequency power for the acceleration tube 64, able to reduce the changing of the energy of the electron beam 57 generated by the acceleration tube 64, and able to reduce the changing of the energy (energy distribution) and intensity of the therapeutic radiation 23, by controlling the klystron 5 based on the shape and the status of the waveguide.

In addition, the control table 104 is able to further relate only an aggregation of rotation angles of the rotary joint 75 to the controlled variable 109, independent from the transformation of the flexible waveguide tubes 74, 86, and 87. The flexible waveguide tube has a small range of flexibility and stretching, that is, a small range where the status can change, and the changing of the transmission efficiency by the transformation is sufficiently small. As a result, by controlling the klystron 5 based on the rotation angle of the rotary joint 75 when the changing of the transmission efficiency by the transformation of the flexible waveguide tubes 74, 86, and 87 is sufficiently small enough to be ignored, the control apparatus 7 is able to supply high frequency wave having small changing of the high-frequency power for the acceleration tube 64, able to reduce the changing of the energy of the electron beam 57 generated by the acceleration tube 64, and able to reduce the changing of the energy (energy distribution) and intensity of the therapeutic radiation 23. At this time, the radiotherapy system can be manufactured in low cost since the evolution angle sensor 6-1, the pan angle sensor 6-3, the tilt angle sensor 6-4 are not required to be provided further.

Further another embodiment of the radiotherapy system according to the present invention does not include the control apparatus 7 according to the above described embodiment. Such radiotherapy system is more suitable than the radiotherapy system 1 according to the above described embodiment when a magnitude of the changing of the transmission efficiency can be sufficiently reduced by the circulator 77 although the magnitude of the changing of the transmission efficiency of the waveguide 8 cannot be reduced more than the above-described radiotherapy system 1.

In further another embodiment of the radiotherapy system according to the present invention, the waveguide 8 in the embodiments described above is replaced by another waveguide (not shown). The waveguide includes a plurality of rotary joints (not shown) and a plurality of circulators (not shown). One of the plurality of the circulators is arranged between a rotary joint closest to the acceleration tube 64 in the plurality of the rotary joints and the acceleration tube 64. The remaining circulators in the plurality of the circulators are arranged between two adjoining rotary joints in the plurality of the rotary joints. When the waveguide is provided with the plurality of the rotary joints, negation of high frequency waves and wave distortions occur in each of the plurality of the rotary joints. The waveguide prevents the negation of high frequency waves and wave distortions generated in each of the plurality of the rotary joints by providing the plurality of the rotary joints and the plurality of the circulators in such manner as described above, and is able to reduce the changing of the high-frequency power supplied for the acceleration tube 64.

In addition, the circulator 77 can be replaced by other non-reciprocal circuit element for effectively attenuating the reflected high-frequency wave progressing in the waveguide from the acceleration tube 64 to the klystron 5 compared to the progressing high-frequency wave progressing in the waveguide 8 from the klystron 5 to the acceleration tube 64. An isolator is exemplified as the non-reciprocal circuit element. The isolator is able to reduce the magnitude of the changing of the transmission efficiency similar to the circulator. The circulator is more suitable to be applied for the radiotherapy system 1 according to the present invention than the isolator since having large heat removal performance compared to the isolator.

Figure 14:
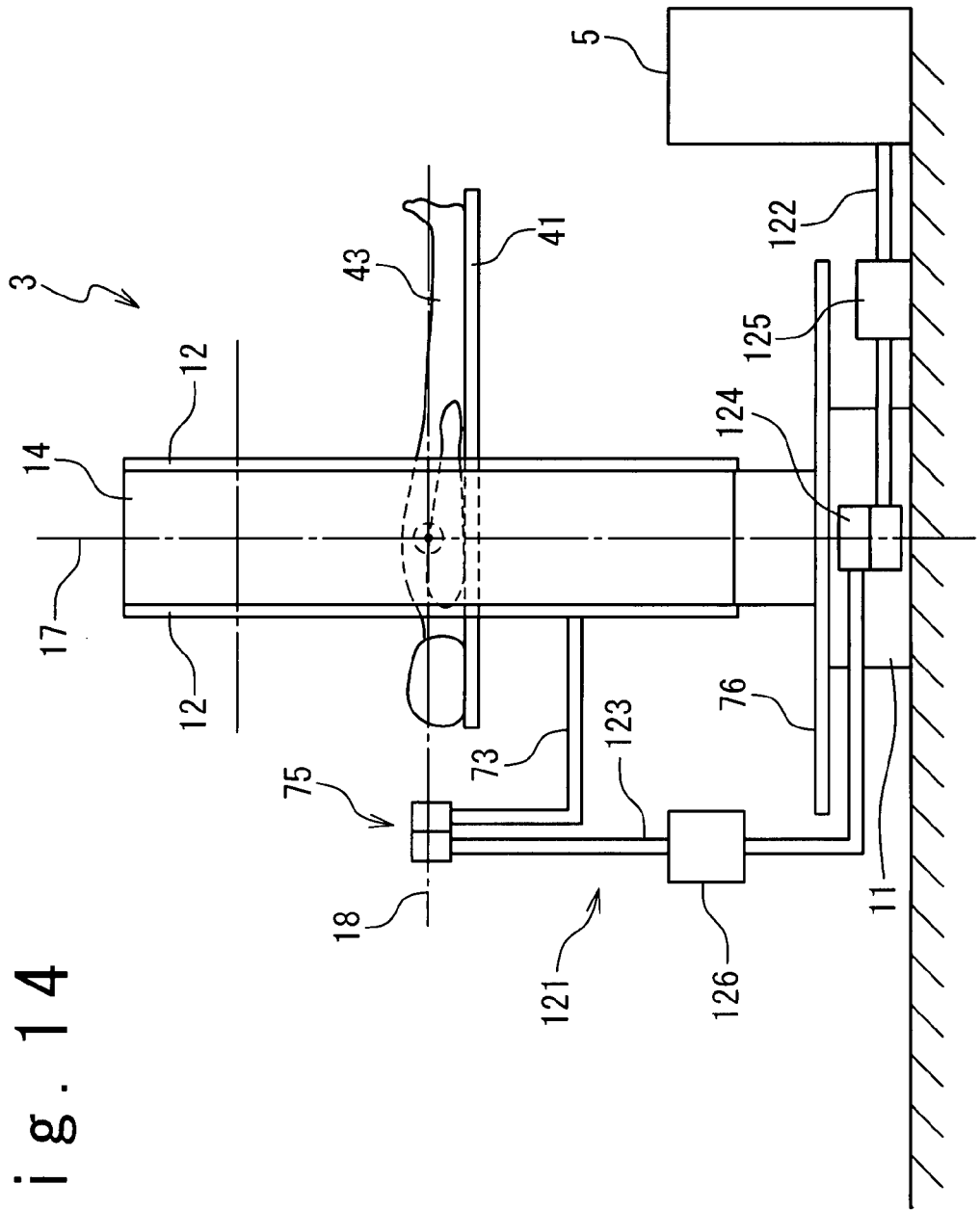
FIG. 14 is a side view showing another waveguide in the embodiment.

In further another embodiment of the radiotherapy system according to the present invention, the waveguide 8 in the embodiments described above is replaced by another waveguide. As shown in FIG. 14, in the waveguide 121, the secured waveguides 71 and 72 and the flexible waveguide 74 in the waveguide 8 according to the above described embodiment are replaced by secured waveguides 122 and 123, a rotary joint 124, and circulators 125 and 126. The secured waveguide 122 forms a waveguide which can not be transformed, is supported by the base, and is connected to the klystron 5 at one end thereof. The secured waveguide 123 forms a waveguide which can not be transformed, and is supported by the turntable 76. The rotary joint 124 is arranged on the rotation axis 17. The rotary joint 124 is connected to the secured waveguide 122 at one end thereof, and connected to the secured waveguide 123 at another end thereof. Similar to the rotary joint 75, the rotary joint 124 rotatably connects the secured waveguide 122 with the secured waveguide 123 centering around the rotation axis 17 so as to transmit high frequency wave between the secured waveguide 122 and the secured waveguide 123.

The circulator 125 is arranged in the middle of the secured waveguide 122. Similar to the circulator 77, the circulator 125 attenuates the reflected wave progressing from the acceleration tube 64 to the klystron 5 compared to the high frequency wave progressing in the secured waveguide 122 from the klystron 5 to the acceleration tube 64. The circulator 126 is arranged in the middle of the secured waveguide 123. Similar to the circulator 77, the circulator 126 attenuates the reflected wave progressing from the acceleration tube 64 to the klystron 5 compared to the high frequency wave progressing in the secured waveguide 123 from the klystron 5 to the acceleration tube 64.

The rotary joints 75 and 124 reflect a part of the entered high frequency wave. A magnitude of the reflection is larger than that of the secured waveguide, and depends on a magnitude of the transformation (rotation angle) of the waveguide by the rotary joint 75 and 124. The circulator 125 reduces a reflected wave entering the klystron 5 to prevent a negative effect caused by the high frequency wave entering the klystron 5. The circulator 126 and the circulator 77 are able to prevent a negation of a high frequency wave progressing to the acceleration tube 64 and the reflected wave, prevent generation of wave distortion of the high frequency wave, and reduce the changing of the transmission efficiency of the waveguide 121. That is to say, an aim to provide the circulator 126 and the circulator 77 is different from an aim to provide the circulator 125.

Similar to when the radiotherapy system 1 includes the waveguide 8, even when the radiotherapy system 1 includes the waveguide 121, the control apparatus 7 is able to control the klystron 5, and to control a dose of the therapeutic radiation 23 with higher precision.

Figure 15:
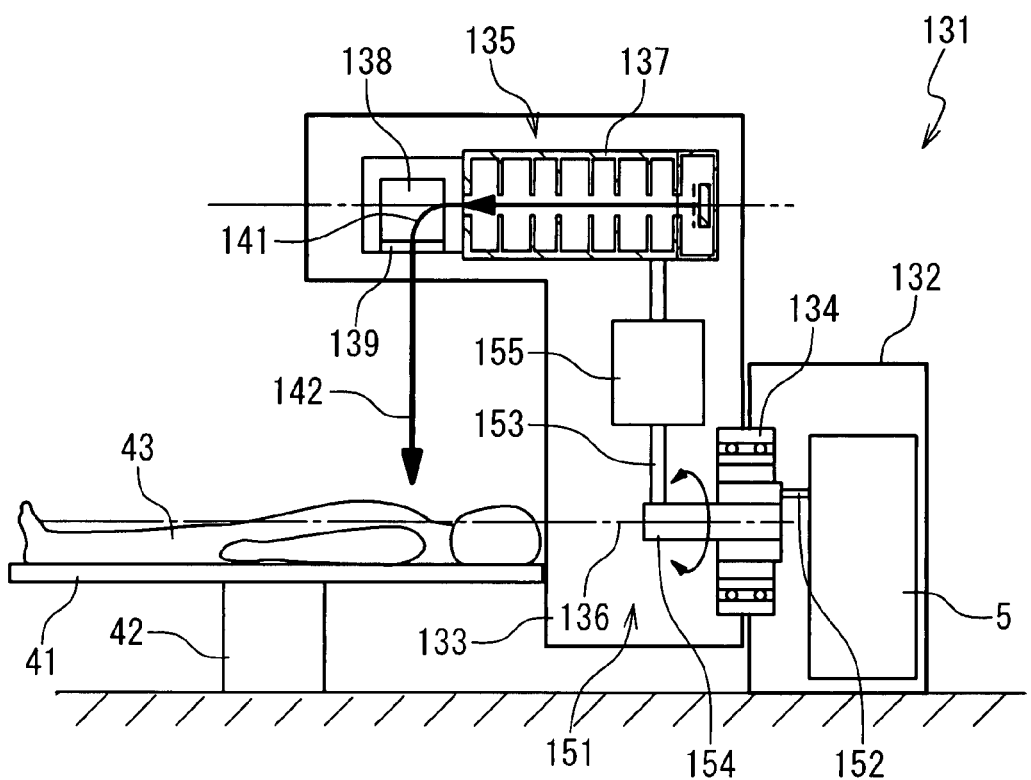
FIG. 15 is a side view showing another radiotherapy apparatus in the embodiment.

In further another embodiment of the radiotherapy system according to the present invention, the radiotherapy apparatus 3 in the embodiments described above is replaced by another radiotherapy apparatus. As shown in FIG. 15, the radiotherapy apparatus 131 includes support members 132 and 133, a bearing 134, and an irradiation head 135. The support member 132 is supported by the base supporting the klystron 5. The bearing 134 rotatably supports the support member 133 centering around the rotation axis 136 against the support member 132. The rotation axis 136 is parallel with a horizontal direction. The support member 133 supports the irradiation head 135.

The irradiation head 135 includes an acceleration unit 137, a bending magnet 138, and a target 139. The acceleration unit 137 emits an accelerated electron beam 141. A direction of the emission of the electron beam 141 is parallel with the rotation axis 136. The bending magnet 138 generates a magnetic field to bend the direction of the electron beam 141. The direction is vertical with the rotation axis 136. The target 139 is made of a material with high atomic number (tungsten, tungsten alloy, and the like), and emits a therapeutic radiation 142 generated by the bremsstrahlung caused by emission of the electron beam 141.

The radiotherapy apparatus 131 further includes a waveguide 151. The waveguide 151 includes secured waveguides 152 and 153, a rotary joint 154, and a circulator 155. The secured waveguide 152 forms a waveguide which can not be transformed, is supported by the support member 132, and is connected to the klystron 5 at one end thereof. The secured waveguide 153 forms a waveguide which can not be transformed, and is supported by the support member 133. The rotary joint 154 is arranged so as to overlap the rotation axis 136. The rotary joint 154 is connected to the secured waveguide 152 at one end thereof, and connected to the secured waveguide 153 at another end thereof. Similar to the rotary joint 75, the rotary joint 154 rotatably connects the secured waveguide 152 with the secured waveguide 153 centering around the rotation axis 136 so as to transmit high frequency wave between the secured waveguide 152 and the secured waveguide 153.

The circulator 155 is arranged in the middle of the secured waveguide 153. Similar to the circulator 77, the circulator 155 attenuates the reflected wave progressing from the acceleration tube 64 to the klystron 5 compared to the high frequency wave progressing in the secured waveguide 153 from the klystron 5 to the acceleration tube 64. The circulator 155 is able to prevent a negation of a high frequency wave progressing to the acceleration tube 64 and the reflected wave, to prevent generation of wave distortion of the high frequency wave, and to reduce the changing of the transmission efficiency of the waveguide tube 151.

The control apparatus 7 is able to control a dose of the therapeutic radiation 23 with higher precision by collecting a status of the waveguide 151 and controlling the klystron 5 based on the status similar to when the radiotherapy system 1 includes the waveguide 8.

Figure 16:
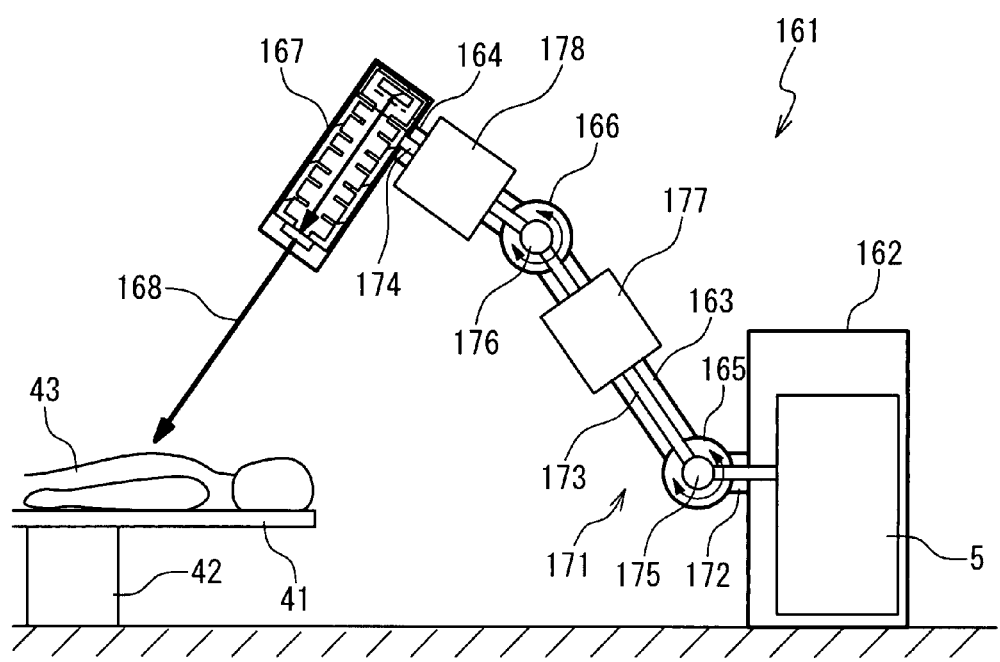
FIG. 16 is a side view showing further another radiotherapy apparatus in the embodiment.

In further another embodiment of the radiotherapy system according to the present invention, the radiotherapy apparatus 3 in the embodiments described above is replaced by another radiotherapy apparatus. As shown in FIG. 16, the radiotherapy apparatus 161 includes support members 162, 163, and 164, bearings 165 and 166, and an irradiation head 167. The support member 162 is supported by the base supporting the klystron 5. The bearing 165 rotatably supports the support member 163 against the support member 162. The bearing 166 rotatably supports the support member 164 against the support member 163. The support member 164 supports the irradiation head 167.

The radiotherapy apparatus 161 further includes a waveguide 171. The waveguide 171 includes secured waveguides 172, 173, and 174, and rotary joints 175 and 176. The secured waveguide 172 forms a waveguide which can not be transformed, is supported by the support member 162, and is connected to the klystron 5 at one end thereof. The rotary joint 175 is arranged so as to overlap the rotation axis of the bearing 165. The rotary joint 175 is connected to the secured waveguide 172 at one end thereof, and connected to the secured waveguide 173 at another end thereof. Similar to the rotary joint 75, the rotary joint 175 rotatably connects the secured waveguide 172 with the secured waveguide 173 centering around the rotation axis of the bearing 165 so as to transmit a high frequency wave between the secured waveguide 172 and the secured waveguide 173.

The secured waveguide 173 forms a waveguide which can not be transformed, is supported by the support member 163. The rotary joint 176 is arranged so as to overlap the rotation axis of the bearing 166. The rotary joint 176 is connected to the secured waveguide 173 at one end thereof, and connected to the secured waveguide 174 at another end thereof. Similar to the rotary joint 75, the rotary joint 176 rotatably connects the secured waveguide 173 with the secured waveguide 174 centering around the rotation axis of the bearing 166 so as to transmit a high frequency wave between the secured waveguide 173 and the secured waveguide 174. The secured waveguide 174 forms a waveguide which can not be transformed, is supported on the support member 164, and is connected to the irradiation head 167 at one end thereof. The irradiation head 167 emits a therapeutic radiation 168 by using a high frequency wave transmitted from the klystron 5 via the waveguide 171.

The waveguide 171 further includes a circulator 177 and a circulator 178. The circulator 177 is arranged in the middle of the secured waveguide 173. Similar to the circulator 77, the circulator 177 attenuates the reflected wave progressing from the irradiation head 167 to the klystron 5 compared to the high frequency wave progressing in the secured waveguide 173 from the klystron 5 to the irradiation head 167. The circulator 178 is arranged in the middle of the secured waveguide 174. Similar to the circulator 77, the circulator 178 attenuates the reflected wave progressing from the irradiation head 167 to the klystron 5 compared to the high frequency wave progressing in the secured waveguide 174 from the klystron 5 to the irradiation head 167. The circulator 177 and the circulator 178 are able to prevent a negation of a high frequency wave progressing to the acceleration tube 64 and the reflected wave, to prevent generation of wave distortion of the high frequency wave, and to reduce the changing of the transmission efficiency of the waveguide 171.

The control apparatus 7 is able to control a dose of the therapeutic radiation 23 with higher precision by collecting a status of the waveguide tube 171 and controlling the klystron 5 based on the status similar to when the radiotherapy system 1 includes the waveguide 8.

Figure 17:
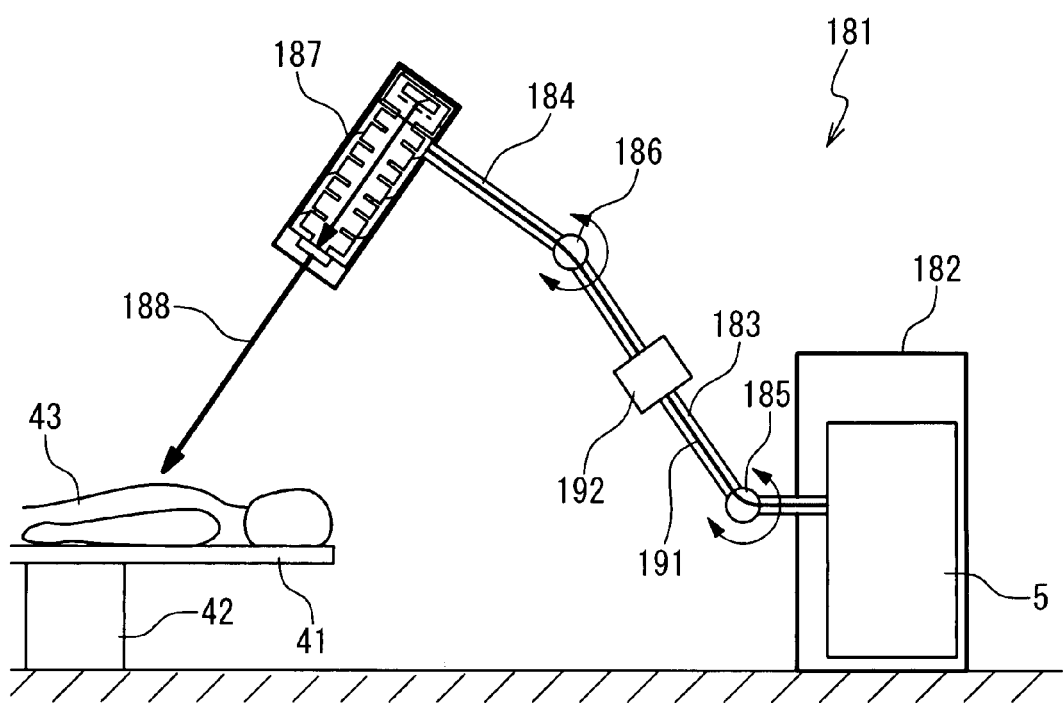
FIG. 17 is a side view showing further another radiotherapy apparatus in the embodiment.

In further another embodiment of the radiotherapy system according to the present invention, the radiotherapy apparatus 3 in the embodiments described above is replaced by another radiotherapy apparatus. As shown in FIG. 17, the radiotherapy apparatus 181 includes support members 182, 183, and 184, bearings 185 and 186, and an irradiation head 187. The support member 182 is supported by the base supporting the klystron 5. The bearing 185 rotatably supports the support member 183 against the support member 182. The bearing 186 rotatably supports the support member 184 against the support member 183. The support member 184 supports the irradiation head 187.

The radiotherapy apparatus 181 further includes a flexible waveguide 191 and a circulator 192. The flexible waveguide 191 is formed in a bellows structure, and forms a bendable and stretchable waveguide. The flexible waveguide 191 is connected to the klystron 5 at one end thereof, and connected to the irradiation head 187 at another end thereof. The circulator 192 is supported by the support member 183, and is arranged in the middle of the flexible waveguide 191. Similar to the circulator 77, the circulator 192 attenuates the reflected wave progressing from the irradiation head 187 to the klystron 5 compared to the high frequency wave progressing in the flexible waveguide 191 from the klystron 5 to the irradiation head 187.

The circulator 192 is able to prevent a negation of a high frequency wave progressing to the irradiation head 187 and the reflected wave, to prevent generation of wave distortion of the high frequency wave, and to reduce the changing of the transmission efficiency of the flexible waveguide tube 191.

The control apparatus 7 is able to control a dose of the therapeutic radiation 23 with higher precision by collecting a status of the waveguide 191 and controlling the klystron 5 based on the status similar to when the radiotherapy system 1 includes the waveguide 8.

A radiotherapy system and an acceleration device according to the present invention are able to prevent a high frequency waves transmitted through a waveguide from being negated each other and distorted in their waveforms, to reduce change of transmission efficiency, to thereby reduce change of energy of charged particles generated by an acceleration tube. As a result, the radiotherapy system is able to reduce change of energy (energy distribution) and intensity of therapeutic radiation and control a dose of the therapeutic radiation with higher-precision.

It is apparent that the present invention is not limited to the above embodiment, but may be modified and changed without departing from the scope and spirit of the invention.

This application is based upon and claims the benefit of priority from Japanese patent applications No. 2007-007331 and 2007-007341 both filed on Jan. 16, 2007, the disclosure of which is incorporated herein in their entirety by reference.

What is claimed is:

1. A radiotherapy system comprising:
   a waveguide configured to transmit a high-frequency wave from a high-frequency power source to an acceleration tube;
   an adjustable waveguide configured to be included in said waveguide and transform a part of said waveguide;
   a non-reciprocal circuit element configured to be provided between said acceleration tube and said adjustable waveguide in said waveguide;
   another adjustable waveguide configured to be included in said waveguide and transform another part of said waveguide between said part and said high-frequency power source; and
   another non-reciprocal circuit element configured to be provided between said part and said another part in said waveguide,
   wherein said acceleration tube accelerates charged particles for generating therapeutic radiation by using said high-frequency wave.

2. The radiotherapy system according to claim 1, wherein said adjustable waveguide includes a rotary joint in which one end is rotatable against another end.

3. The radiotherapy system according to claim 1, wherein said non-reciprocal circuit element includes a circulator.

4. The radiotherapy system according to claim 1, further comprising:
   an apparatus configured to output a status of said waveguide; and
   a control apparatus configured to control said high-frequency power source such that a high-frequency power is supplied to said acceleration tube by using said high-frequency wave, based on said status.

5. A radiotherapy system comprising:
   a waveguide configured to transmit a high-frequency wave from a high-frequency power source to an acceleration tube;
   an adjustable waveguide configured to be included in said waveguide and transform a part of said waveguide;
   a non-reciprocal circuit element configured to be provided between said acceleration tube and said adjustable waveguide in said waveguide;
   another adjustable waveguide configured to be included in said waveguide and transform another part of said waveguide between said part and said high-frequency power source; and
   another non-reciprocal circuit element configured to be provided between said another part of said waveguide and said high-frequency power source in said waveguide, wherein said acceleration tube accelerates charged particles for generating therapeutic radiation by using said high-frequency wave.

6. An acceleration apparatus comprising:
   a waveguide configured to transmit a high-frequency wave from a high-frequency power source to an acceleration tube;
   an adjustable waveguide configured to be included in said waveguide and transform a part of said waveguide;
   a circulator configured to be provided between said acceleration tube and said adjustable waveguide in said waveguide;
   another adjustable waveguide configured to be included in said waveguide and transform another part of said waveguide between said part and said high-frequency power source; and
   another circulator configured to be provided between said another part of said waveguide and said high-frequency power source in said waveguide,
   wherein said acceleration tube accelerates charged particles by using said high-frequency wave.

7. An acceleration apparatus comprising:
   a waveguide configured to transmit a high-frequency wave from a high-frequency power source to an acceleration tube;
   an adjustable waveguide configured to be included in said waveguide and transform a part of said waveguide;

a circulator configured to be provided between said acceleration tube and said adjustable waveguide in said waveguide;

another adjustable waveguide configured to be included in said waveguide and transform another part of said waveguide between said part and said high-frequency power source; and another circulator configured to be provided between said part and said another part in said waveguide, wherein said acceleration tube accelerates charged particles by using said high-frequency wave.

8. A radiotherapy system comprising:

an apparatus configured to output a status of a waveguide which transmits a high-frequency wave from a high-frequency power source to an acceleration tube; and a control apparatus configured to control said high-frequency power source such that high-frequency power is supplied to said acceleration tube by using said high-frequency wave, based on said status, wherein said acceleration tube accelerates charged particles for generating therapeutic radiation by using said high-frequency wave, wherein said waveguide includes:

an adjustable waveguide configured to transform a part of said waveguide, wherein said status includes:

a shape of said waveguide.

9. The radiotherapy system according to claim 8, wherein said apparatus measures said status and outputs said measured status.

10. The radiotherapy system according to claim 8, further comprising:

a driving apparatus configured to move said acceleration tube, wherein said apparatus further controls said driving apparatus based on said status.

11. The radiotherapy system according to claim 8, wherein said adjustable waveguide includes:

a rotary joint configured to have one end rotatable against another end, wherein said status includes:

an angle between said one end and said another end.

12. The radiotherapy system according to claim 8, wherein said adjustable waveguide includes:

a first adjustable waveguide, and a second adjustable waveguide, wherein said status includes:

a shape of said first adjustable waveguide, and a shape of said second adjustable waveguide.

13. The radiotherapy system according to claim 8, wherein said status includes:

a high-frequency power supplied to said acceleration tube.

14. The radiotherapy system according to claim 8, wherein said status includes:

a shape of said waveguide, and a high-frequency power supplied to said acceleration tube.

15. An acceleration apparatus comprising:

an apparatus configured to output a status of a waveguide which transmits a high-frequency wave from a high-frequency power source to an acceleration tube; and a control apparatus configured to control said high-frequency power source such that high-frequency power is supplied to said acceleration tube, based on said status, wherein said acceleration tube accelerates charged particles by using said high-frequency wave, wherein said waveguide includes:

an adjustable waveguide configured to transform a part of said waveguide, wherein said status includes:

a shape of said waveguide.

* * * * *